(12) United States Patent
Knopfmacher et al.

(10) Patent No.: US 11,021,732 B2
(45) Date of Patent: Jun. 1, 2021

(54) DEVICES, SYSTEMS AND METHODS TO DETECT VIABLE INFECTIOUS AGENTS IN A FLUID SAMPLE AND SUSCEPTIBILITY OF INFECTIOUS AGENTS TO ANTI-INFECTIVES

(71) Applicant: Avails Medical, Inc., Menlo Park, CA (US)

(72) Inventors: Oren S. Knopfmacher, San Francisco, CA (US); Meike Herget, Woodside, CA (US); Michael D. Laufer, Menlo Park, CA (US); August Estabrook, South San Francisco, CA (US)

(73) Assignee: Avails Medical, Inc., Menlo Park, CA (US)

( * ) Notice: Subject to any disclaimer, the term of this patent is extended or adjusted under 35 U.S.C. 154(b) by 328 days.

(21) Appl. No.: 16/241,691

(22) Filed: Jan. 7, 2019

(65) Prior Publication Data

US 2019/0136290 A1    May 9, 2019

Related U.S. Application Data

(63) Continuation of application No. 15/482,307, filed on Apr. 7, 2017, now Pat. No. 10,174,356.

(60) Provisional application No. 62/343,564, filed on May 31, 2016.

(51) Int. Cl.
*G01N 27/27* (2006.01)
*C12Q 1/18* (2006.01)
(Continued)

(52) U.S. Cl.
CPC .............. *C12Q 1/18* (2013.01); *C12Q 1/006* (2013.01); *C12Q 1/025* (2013.01); *C12Q 1/04* (2013.01);
(Continued)

(58) Field of Classification Search
CPC ... B01L 3/502715; C12Q 1/006; C12Q 1/025; C12Q 1/04; C12Q 1/18; G01N 27/27;
(Continued)

(56) References Cited

U.S. PATENT DOCUMENTS

| 4,236,893 A | 12/1980 | Rice |
| 4,314,821 A | 2/1982 | Rice |

(Continued)

FOREIGN PATENT DOCUMENTS

| EP | 0235024 | 9/1987 |
| EP | 1460130 | 9/2004 |

(Continued)

OTHER PUBLICATIONS

Dortet, Laurent et al., "Bloodstream Infections Caused by *Pseudomonas* spp.: How to Detect Carbapenemase Producers Directly from Blood Cultures", Journal of Clinical Microbiology, 52(4):1269-1273, Apr. 2014.

(Continued)

*Primary Examiner* — Jennifer Wecker
(74) *Attorney, Agent, or Firm* — Levine Bagade Han LLP

(57) ABSTRACT

Various devices, systems and methods for detecting infectious agents or determining a susceptibility of an infectious agent to an anti-infective are described herein. One example method comprises introducing a fluid sample to a surface; exposing the surface to a solution; sampling the solution after exposing the solution to the surface; and detecting a change in an electrical characteristic of a sensing device exposed to the solution sampled corresponding to a presence of the infectious agent in the fluid sample.

21 Claims, 20 Drawing Sheets

(51) Int. Cl.

| | | |
|---|---|---|
| C12Q 1/02 | (2006.01) | |
| C12Q 1/04 | (2006.01) | |
| G01N 27/416 | (2006.01) | |
| G01N 27/327 | (2006.01) | |
| G01N 33/50 | (2006.01) | |
| C12Q 1/00 | (2006.01) | |
| B01L 3/00 | (2006.01) | |

(52) U.S. Cl.
CPC ......... *G01N 27/27* (2013.01); *G01N 27/3273* (2013.01); *G01N 27/3275* (2013.01); *G01N 33/5011* (2013.01); *B01L 3/502715* (2013.01); *G01N 27/3272* (2013.01)

(58) Field of Classification Search
CPC ........... G01N 27/3272; G01N 27/3273; G01N 27/3275; G01N 33/5011; H05K 1/0233; H05K 1/0298; H05K 2201/10015; H05K 2201/10689; H05K 9/0039
See application file for complete search history.

(56) References Cited

U.S. PATENT DOCUMENTS

| | | | |
|---|---|---|---|
| 4,448,534 A * | 5/1984 | Wertz | C12M 41/36 356/435 |
| 4,735,906 A | 4/1988 | Bastiaans | |
| 4,767,719 A | 8/1988 | Finlan | |
| 4,789,804 A | 12/1988 | Karube et al. | |
| 4,822,566 A | 4/1989 | Newman | |
| 4,965,193 A | 10/1990 | Chen | |
| 4,977,247 A | 12/1990 | Fahnestock et al. | |
| 5,064,756 A | 11/1991 | Carr et al. | |
| 5,077,210 A | 12/1991 | Eigler et al. | |
| 5,111,221 A | 5/1992 | Fare et al. | |
| 5,172,332 A | 12/1992 | Hungerford et al. | |
| 5,182,005 A | 1/1993 | Schwiegk et al. | |
| 5,447,845 A | 9/1995 | Chu et al. | |
| 5,821,399 A | 10/1998 | Zelin | |
| 5,922,537 A | 7/1999 | Ewart et al. | |
| 6,280,586 B1 | 8/2001 | Wolf et al. | |
| 6,368,795 B1 | 4/2002 | Hefti | |
| 6,391,558 B1 | 5/2002 | Henkens et al. | |
| 6,548,263 B1 | 4/2003 | Kapur et al. | |
| 6,548,311 B1 | 4/2003 | Knoll | |
| 6,780,307 B2 | 8/2004 | Kidwell | |
| 6,863,792 B1 | 3/2005 | Madou et al. | |
| 8,508,100 B2 | 8/2013 | Lee et al. | |
| 8,728,844 B1 | 5/2014 | Liu et al. | |
| 9,377,456 B1 | 6/2016 | Herget et al. | |
| 9,702,847 B2 | 7/2017 | Herget et al. | |
| 9,766,201 B2 | 9/2017 | Herget et al. | |
| 9,944,969 B2 | 4/2018 | Knopfmacher et al. | |
| 9,963,733 B2 | 5/2018 | Knopfmacher et al. | |
| 10,060,916 B2 | 8/2018 | Knopfmacher | |
| 10,174,356 B2 | 1/2019 | Knopfmacher et al. | |
| 10,254,245 B2 | 4/2019 | Knopfmacher et al. | |
| 2002/0127623 A1 | 9/2002 | Minshull et al. | |
| 2003/0073071 A1 | 4/2003 | Fritz et al. | |
| 2003/0109056 A1 | 6/2003 | Vossmeyer et al. | |
| 2003/0119208 A1 | 6/2003 | Yoon et al. | |
| 2006/0102935 A1 | 5/2006 | Yitzchaik et al. | |
| 2006/0197118 A1 | 9/2006 | Migliorato et al. | |
| 2006/0246426 A1 | 11/2006 | Woodbury et al. | |
| 2006/0286548 A1 | 12/2006 | Liposky | |
| 2007/0072187 A1 | 3/2007 | Blok et al. | |
| 2008/0012007 A1 | 1/2008 | Li et al. | |
| 2008/0199863 A1 | 8/2008 | Haake et al. | |
| 2009/0008247 A1 | 1/2009 | Chen et al. | |
| 2009/0020438 A1 | 1/2009 | Hodges | |
| 2009/0273354 A1 | 11/2009 | Dhirani et al. | |
| 2010/0025660 A1 | 2/2010 | Jain et al. | |
| 2010/0137143 A1 | 6/2010 | Rothberg et al. | |
| 2010/0194409 A1 | 8/2010 | Gao et al. | |
| 2011/0068372 A1 | 3/2011 | Ren et al. | |
| 2011/0306032 A1 | 12/2011 | Galiano et al. | |
| 2012/0032235 A1 | 2/2012 | Bikumandla | |
| 2012/0077692 A1 | 3/2012 | Hassibi et al. | |
| 2012/0088682 A1 | 4/2012 | Rothberg et al. | |
| 2012/0143027 A1 | 6/2012 | Phillips et al. | |
| 2012/0153262 A1 | 6/2012 | Paranjape et al. | |
| 2012/0153407 A1 | 6/2012 | Chang et al. | |
| 2012/0168306 A1 | 7/2012 | Hassibi et al. | |
| 2012/0208291 A1 | 8/2012 | Davis et al. | |
| 2012/0261274 A1 | 10/2012 | Rearick et al. | |
| 2012/0256166 A1 | 11/2012 | Chen et al. | |
| 2012/0279859 A1 | 11/2012 | Rothberg et al. | |
| 2013/0089883 A1 | 4/2013 | Dallenne et al. | |
| 2013/0089932 A1 | 4/2013 | Wu et al. | |
| 2013/0096013 A1 | 4/2013 | Esfandyarpour et al. | |
| 2013/0105868 A1 | 5/2013 | Kalnitsky et al. | |
| 2013/0217063 A1 | 8/2013 | Metzger et al. | |
| 2014/0011218 A1 | 1/2014 | Han et al. | |
| 2014/0057339 A1 | 2/2014 | Esfandyarpour et al. | |
| 2014/0134656 A1 | 5/2014 | Dortet et al. | |
| 2014/0191294 A1 | 7/2014 | Bikumandla et al. | |
| 2014/0231256 A1 | 8/2014 | Packingham et al. | |
| 2014/0349005 A1 | 11/2014 | Everett et al. | |
| 2015/0355129 A1 * | 12/2015 | Knopfmacher | G01N 27/3272 205/792 |
| 2016/0039657 A1 | 2/2016 | Jain et al. | |
| 2016/0187332 A1 | 6/2016 | Herget et al. | |
| 2016/0187334 A1 | 6/2016 | Herget et al. | |
| 2016/0208306 A1 | 7/2016 | Pollak et al. | |
| 2016/0209356 A1 | 7/2016 | Herget et al. | |
| 2016/0266102 A1 | 9/2016 | Knopfmacher | |
| 2017/0058313 A1 | 3/2017 | Knopfmacher et al. | |
| 2017/0059508 A1 | 3/2017 | Knopfmacher et al. | |
| 2017/0212075 A1 | 7/2017 | Knopfmacher et al. | |
| 2017/0336348 A1 | 11/2017 | Herget et al. | |
| 2017/0342459 A1 | 11/2017 | Knopfmacher et al. | |
| 2018/0195106 A1 | 7/2018 | Knopfmacher et al. | |
| 2018/0364221 A1 | 12/2018 | Knopfmacher | |

FOREIGN PATENT DOCUMENTS

| | | | |
|---|---|---|---|
| JP | 1988-066454 | 3/1988 | |
| JP | 2006-511818 | 4/2006 | |
| JP | 2011-58900 | 3/2011 | |
| JP | 2011-085038 | 11/2012 | |
| WO | WO 2003/044530 | 5/2003 | |
| WO | WO 2003/052097 | 6/2003 | |
| WO | WO 2004/077052 | 9/2004 | |
| WO | WO 2007/035814 | 3/2007 | |
| WO | WO 2010/062001 | 6/2010 | |
| WO | WO 2012/078340 | 6/2012 | |
| WO | WO 2013/096404 | 6/2013 | |
| WO | WO 2014/080292 | 5/2014 | |
| WO | WO 2014/134431 | 9/2014 | |
| WO | WO-2014134431 A1 * | 9/2014 | ....... G01N 33/48735 |
| WO | WO 2015/077632 | 5/2015 | |
| WO | WO 2015/188002 | 12/2015 | |
| WO | WO 2016/005743 | 1/2016 | |
| WO | WO 2016/028233 | 2/2016 | |
| WO | WO 2016/061453 | 4/2016 | |
| WO | WO 2016/109569 | 7/2016 | |
| WO | WO 2017/035393 | 3/2017 | |
| WO | WO 2017/107333 | 6/2017 | |
| WO | WO 2017/132095 | 8/2017 | |
| WO | WO 2017/209839 | 12/2017 | |
| WO | WO 2018/111234 | 6/2018 | |
| WO | WO 2018/145338 | 8/2018 | |
| WO | WO 2019/005296 | 1/2019 | |
| WO | WO 2019/070739 | 4/2019 | |

OTHER PUBLICATIONS

Dortet, Laurent et al., "CarbAcineto NP Test for Rapid Detection of Carbapenemase-Producing *Acinetobacter* spp.", Journal of Clinical Microbiology, 52(7):2359-2364, Jul. 2014.
Dortet, Laurent et al., "Evaluation of the RAPIDECw CARBA NP, the Rapid CARB Screenw and the Carba NP test for biochemical

(56) References Cited

OTHER PUBLICATIONS detection of carbapenemase-producing Enterobacteriaceae", J Antimicrob Chemother, 70:3014-3022, 2015.

Dortet, Laurent et al., "Further Proofs of Concept for the Carba NP Test", Antimicrobial Agents and Chemotherapy, 58(2):1269, Feb. 2014.

Dortet, Laurent et al., "Rapid Identification of Carbapenemase Types in *Enterobacteriaceae* and *Pseudomonas* spp. by Using a Biochemical Test", Antimicrobial Agents and Chemotherapy, 56(12):6437-6440, Dec. 2012.

Estrela, Pedro et al., "Label-Free Sub-picomolar Protein Detection with Field-Effect Transistors," Analytical Chemistry, vol. 82, No. 9, May 1, 2010, 3531-3536.

Hammock, Mallory L. et al., "Electronic readout ELISA with organic field-effect transistors as a prognostic test for preeclampsia," Advanced Materials, 26: 6138-6144. doi: 10.1002/adma. 201401829.

Kumar et al., "Sensitivity Enhancement Mechanisms in Textured Dielectric Based Electrolyte-Insulator-Semiconductor (EIS) Sensors," *ECS Journal of Solid State Science and Technology*, 4(3):N18-N23 (2015).

Mathias, W. et al., "Selective Sodium Sensing with Gold-Coated Silicon Nanowire Field-Effect Transistors in a Differential Setup," ACS Nano 7, 5978-5983 (2013).

Nordmann, Patrice et al., "Strategies for identification of carbapenemase-producing Enterobacteriaceae", J Antimicrob Chemother, 68:487-489, 2013.

Poghossian et al., "Penicillin Detection by Means of Field-Effect Based Sensors: EnFET, Capacitive EIS Sensor or LAPS?", *Sensors and Actuators B*, 78:237 (2001).

Poirel, Laurent et al., "Rapidec Carba NP Test for Rapid Detection of Carbapenemase Producers", Journal of Clinical Microbiology, 53(9):3003-3008, Sep. 2015.

Salm, Eric et al., "Electrical Detection of Nucleic Acid Amplification Using an On-Chip Quasi-Reference Electrode and a PVC REFET," dx.doi.org/10.1021/ac500897t, *Anal. Chem.*, 2014, 86, 6968-6975.

Schoning, Michael J., "'Playing Around' with Field-Effect Sensors on the Basis of EIS Structures, LAPS and ISFETs," *Sensors*, 5:126-138 (2005).

Pourciel-Gouzy M L et al: "pH-ChemFET-based analysis devices for the bacterial activity monitoring." Sensors and Actuators B: Chemical: International Journal Devoted to Research and Development of Physical and Chemical Transducers, Elsevier BV, NL, vol. 134, No. 1 Aug. 28, 2008, pp. 339-344.

Oliu et al., "Impedimetric Sensors for Bacteria Detection," Biosensors—Micro and Nanoscale Applications, Chpt. 9 (Sep. 2015) p. 257-288.

\* cited by examiner

STEP 11E(b)          STEP 11E(a)

STEP 11E(d)　　　　　　STEP 11E(c)

STEP 11E(f)  STEP 11E(e)

```
                              START
                                │
                                ▼
         ┌─────────────────────────────────────────────────┐ ─ 1502
         │ INTRODUCE A FLUID SAMPLE TO A FIRST SURFACE AND A SECOND SURFACE │
         └─────────────────────────────────────────────────┘
                                │
                                ▼
         ┌─────────────────────────────────────────────────┐ ─ 1504
         │ EXPOSE THE FIRST SURFACE COMPRISING THE INFECTIOUS AGENT TO A FIRST SOLUTION │
         └─────────────────────────────────────────────────┘
                                │
                                ▼
         ┌─────────────────────────────────────────────────┐ ─ 1506
         │ EXPOSE THE SECOND SURFACE COMPRISING THE INFECTIOUS AGENT TO A SECOND SOLUTION, WHEREIN THE SECOND SOLUTION COMPRISES AN ANTI-INFECTIVE │
         └─────────────────────────────────────────────────┘
                                │
                                ▼
         ┌─────────────────────────────────────────────────┐ ─ 1508
         │ SAMPLE THE FIRST SOLUTION AFTER EXPOSING THE FIRST SOLUTION TO THE FIRST SURFACE │
         └─────────────────────────────────────────────────┘
                                │
                                ▼
         ┌─────────────────────────────────────────────────┐ ─ 1510
         │ SAMPLE THE SECOND SOLUTION AFTER EXPOSING THE SECOND SOLUTION TO THE SECOND SURFACE │
         └─────────────────────────────────────────────────┘
                                │
                                ▼
         ┌─────────────────────────────────────────────────┐ ─ 1512
         │ MONITOR A FIRST ELECTRICAL CHARACTERISTIC OF A FIRST SENSING DEVICE EXPOSED TO THE FIRST SOLUTION SAMPLED │
         └─────────────────────────────────────────────────┘
                                │
                                ▼
         ┌─────────────────────────────────────────────────┐ ─ 1514
         │ MONITOR A SECOND ELECTRICAL CHARACTERISTIC OF A SECOND SENSING DEVICE EXPOSED TO THE SECOND SOLUTION SAMPLED │
         └─────────────────────────────────────────────────┘
                                │
                                ▼
         ┌─────────────────────────────────────────────────┐ ─ 1516
         │ COMPARE THE FIRST ELECTRICAL CHARACTERISTIC AND THE SECOND ELECTRICAL CHARACTERISTIC TO ASSESS THE SUSCEPTIBILITY OF THE INFECTIOUS AGENT TO THE ANTI-INFECTIVE │
         └─────────────────────────────────────────────────┘
```

START

1602 INTRODUCE A FLUID SAMPLE TO A FIRST SURFACE AND A SECOND SURFACE

1604 EXPOSE THE FIRST SURFACE COMPRISING THE INFECTIOUS AGENT TO A FIRST SOLUTION

1606 EXPOSE THE SECOND SURFACE COMPRISING THE INFECTIOUS AGENT TO A SECOND SOLUTION, WHEREIN THE SECOND SOLUTION COMPRISES AN ANTI-INFECTIVE

1608 SAMPLE THE FIRST SOLUTION AFTER EXPOSING THE FIRST SOLUTION TO THE FIRST SURFACE

1610 SAMPLE THE SECOND SOLUTION AFTER EXPOSING THE SECOND SOLUTION TO THE SECOND SURFACE

1612 MONITOR A FIRST ELECTRICAL CHARACTERISTIC OF A SENSING DEVICE EXPOSED TO THE FIRST SOLUTION SAMPLED

1614 MONITOR A SECOND ELECTRICAL CHARACTERISTIC OF THE SENSING DEVICE EXPOSED TO THE SECOND SOLUTION SAMPLED

1616 COMPARE THE FIRST ELECTRICAL CHARACTERISTIC AND THE SECOND ELECTRICAL CHARACTERISTIC TO ASSESS THE SUSCEPTIBILITY OF THE INFECTIOUS AGENT TO THE ANTI-INFECTIVE

FIGURE 16

DEVICES, SYSTEMS AND METHODS TO DETECT VIABLE INFECTIOUS AGENTS IN A FLUID SAMPLE AND SUSCEPTIBILITY OF INFECTIOUS AGENTS TO ANTI-INFECTIVES

CROSS-REFERENCE TO RELATED APPLICATION

This application is a continuation of U.S. patent application Ser. No. 15/482,307 filed on Apr. 7, 2017, now U.S. Pat. No. 10,174,356, which claims the benefit of U.S. Provisional Application No. 62/343,564 filed on May 31, 2016, the contents of which are incorporated herein by reference in their entireties.

FIELD OF THE INVENTION

The present disclosure relates generally to in vitro detection of infectious agents and in vitro determination of the susceptibility of infectious agents to anti-infectives. More specifically, the present disclosure relates to devices, systems, and methods to detect viable infectious agents in a fluid sample and determine the susceptibility of such infectious agents to anti-infectives.

BACKGROUND

Infections caused by anti-infective resistant infectious agents or microbes are a significant problem for healthcare professionals in hospitals, nursing homes, and other healthcare environments. For example, such infections can lead to a potentially life-threatening complication known as sepsis where chemicals released into the bloodstream by an infectious agent can trigger a dangerous whole-body inflammatory response as well as a vasoactive response causing fever, low blood pressure, and possibly death. When faced with such an infection, a preferred course of action is for a clinician to use anti-infective compounds judiciously, preferably only those necessary to alleviate the infection. However, what occurs most frequently today is that until the organism is identified and tested for drug sensitivity, broad-spectrum anti-infectives, often multiple drugs, are given to the patient to ensure adequacy of treatment. This tends to result in multiple drug-resistant infectious agents. Ideally, the sensitivity of the infectious agent would be detected soon after its presence is identified. The present disclosure presents devices, systems, and methods for accomplishing this goal.

Existing methods and instruments used to detect anti-infective resistance in infectious agents include costly and labor intensive microbial culturing techniques to isolate the infectious agent and include tests such as agar disk diffusion or broth microdilution where anti-infectives are introduced as liquid suspensions, paper disks, or dried gradients on agar media. However, those methods require manual interpretation by skilled personnel and are prone to technical or clinician error.

While automated inspection of such panels or media can reduce the likelihood of clinician error, current instruments used to conduct these inspections are often costly and require constant maintenance. In addition, current instruments often rely on an optical read-out of the investigated samples requiring bulky detection equipment and access to power supplies. Most importantly, these methods require days to obtain a result, as the infectious agents must reproduce several times in different media prior to being exposed to the anti-infective to determine their susceptibility.

In addition, such methods and instruments often cannot conduct such tests directly on a patient's bodily fluids and require lengthy sample preparation times.

As a result of the above limitations and restrictions, there is a need for improved devices, systems, and methods to quickly and effectively detect anti-infective resistant infectious agents in a patient sample.

SUMMARY

Various devices, systems and methods for detecting viable infectious agents in a fluid sample and determining the susceptibility of such infectious agents to anti-infectives are described herein. In one embodiment, a method of detecting an infectious agent in a fluid sample can include introducing a fluid sample to a surface; exposing the surface to a solution; sampling the solution after exposing the solution to the surface; and detecting a change in an electrical characteristic of a sensing device exposed to the solution sampled corresponding to a presence of the infectious agent in the fluid sample.

In another embodiment, a method of assessing a susceptibility of an infectious agent to an anti-infective can include introducing a fluid sample to a first surface and a second surface; exposing the first surface comprising the infectious agent to a first solution; exposing the second surface comprising the infectious agent to a second solution, wherein at least one of the second surface and the second solution comprises an anti-infective; sampling the first solution after exposing the first solution to the first surface; sampling the second solution after exposing the second solution to the second surface; monitoring a first electrical characteristic of a first sensing device exposed to the first solution sampled; monitoring a second electrical characteristic of a second sensing device exposed to the second solution sampled; and comparing the first electrical characteristic and the second electrical characteristic to assess the susceptibility of the infectious agent to the anti-infective.

In yet another embodiment, a method of assessing a susceptibility of an infectious agent to an anti-infective includes introducing a fluid sample to a first surface and a second surface; exposing the first surface comprising the infectious agent to a first solution; exposing the second surface comprising the infectious agent to a second solution, wherein at least one of the second surface and the second solution comprises an anti-infective; sampling the first solution after exposing the first surface to the first solution; sampling the second solution after exposing the second surface to the second solution; monitoring a first electrical characteristic of a sensing device exposed to the first solution sampled; monitoring a second electrical characteristic of the sensing device exposed to the second solution sampled; and comparing the first electrical characteristic and the second electrical characteristic to assess the susceptibility of the infectious agent to the anti-infective.

BRIEF DESCRIPTION OF THE SEVERAL VIEWS OF THE DRAWINGS

FIG. 15 illustrates an embodiment of a method for detecting a susceptibility of an infectious agent to one or more anti-infectives.

FIG. 16 illustrates another embodiment of a method for determining the susceptibility of an infectious agent to one or more anti-infectives.

DETAILED DESCRIPTION

Variations of the devices, systems, and methods described herein are best understood from the detailed description when read in conjunction with the accompanying drawings. It is emphasized that, according to common practice, the various features of the drawings may not be to scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

Figure 1:
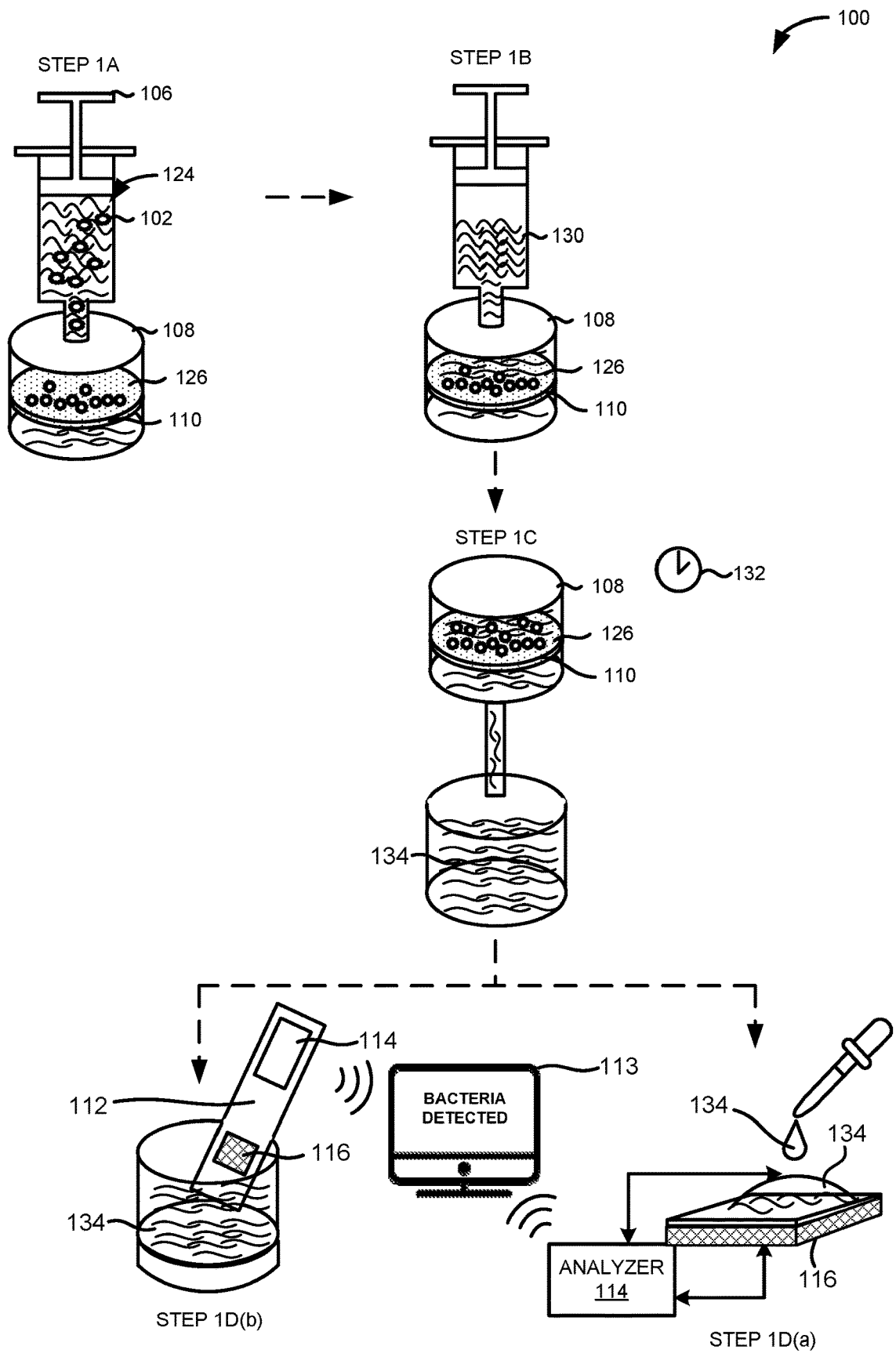
FIG. 1 illustrates one embodiment of a system for detecting infectious agents in a fluid sample.

FIG. 1 illustrates an embodiment of a system 100 for detecting an infectious agent 102 in a fluid sample 124. In one embodiment, the system 100 can comprise a fluid delivery device 106, a filter housing 108 containing a filter 110, a sensing device 116, and a parameter analyzer 114. The sensing device 116 can be located on a substrate 112.

The substrate 112 can be comprised of a polymer or polymeric material, a metal, a ceramic, a semiconductor layer, an oxide layer, an insulator, or a combination thereof. As shown in FIG. 1, the parameter analyzer 114 can be integrated into one device with the sensing device 116. For example, the parameter analyzer 114 can be fabricated on the same substrate 112 as the sensing device 116. In other embodiments, the parameter analyzer 114 can be a stand-alone unit or device coupled to the sensing device 116. The sensing device will be discussed in more detail in the sections that follow.

In some instances, the fluid sample 124 can comprise the infectious agent 102. The fluid sample 124 can include a bodily fluid such as blood, serum, plasma, urine, saliva, joint fluid, semen, wound material, spinal fluid, mucus, or a combination thereof. In other embodiments, the fluid sample 124 can also include an environmental fluid such as liquids sampled from a stream, river, lake, ocean, contamination site, quarantine zone, or emergency area. The fluid sample 124 can also be a food sample.

The infectious agent 102 can be any metabolizing single or multi-cellular organism including a bacteria or fungus. The infectious agent 102 can also be a virus or a prion. In certain embodiments, the infectious agent 102 can be a bacteria selected from the genera comprising of, but not limited to, *Acinetobacter, Aeromonas, Bacillus, Bacteroides, Citrobacter, Enterobacter, Escherichia, Klebsiella, Morganella, Pandoraea, Proteus, Providencia, Pseudomonas, Ralstonia, Raoultella, Salmonella, Serratia, Shewanella, Shigella, Stenotrophomonas, Streptomyces, Staphylococcus, Enterococcus, Clostridium* or any combination thereof. In other embodiments, the infectious agent 102 can be a fungus selected from the genera comprising of, but not limited to, *Candida, Cryptococcus*, or any combination thereof. In another embodiment, the infectious agent 102 can include amoeba. In further embodiments, the infectious agent 102 can be cancer cells.

As illustrated in FIG. 1, the fluid delivery device 106 can deliver or inject the fluid sample 124 into the filter housing 108 in step 1A. In one embodiment, the fluid delivery device 106 can be a pump. For example, the fluid delivery device 106 can be a hydraulic pump, a pneumatic pump, a syringe pump, or a combination thereof. In other embodiments, the fluid delivery device 106 can be an injection cartridge, a microfluidic channel, a pipette, a reaction tube, a capillary, a test tube, a combination thereof, or a portion therein.

The filter housing 108 can be a container or vessel configured to secure or enclose the filter 110. For example, the filter housing 108 can be a protective chamber. The protective chamber can be an electrically isolated environment. The protective chamber can also be a temperature controlled chamber, a light controlled chamber, or a combination thereof.

The filter 110 can have a filter surface 126. The filter 110 can trap or isolate the infectious agent 102 by depositing or delivering the infectious agent 102 onto the filter surface 126. The filter surface 126 can be an external surface, an internal surface extending into the filter 110, or a combination thereof. The filter 110 can be made of, but is not limited to, cellulose acetate, regenerated cellulose, nylon, polystyrene, polyvinylidene fluoride (PVDF), polyethersulfone (PES), polytetrafluorethylene (PTFE), glass microfiber, or a combination thereof.

In one embodiment, the filter 110 can have filter pores of sequentially smaller pore size. For example, the filter 110 can have larger filter pores at the top of the filter and progressively smaller filter pores toward the bottom of the filter. In another embodiment, the filter 110 can have filter pores of a similar pore size throughout the entire filter. In these embodiments, the filter surface 126 can be the surface of the pores. In another embodiment, the filter 110 can be a mesh or matrix structure and the filter surface 126 can be a mesh or matrix surface.

The filter 110 can be a non-clogging filter such as a high-capacity filter. Although not shown in FIG. 1, it is contemplated by this disclosure that the filter 110 can refer to a plurality of filters in a stacked arrangement.

The filter 110 can comprise, carry, or hold the infectious agent 102 when a fluid sample 124 comprising or carrying an infectious agent 102 is introduced to the filter 110. For example, the fluid sample 124 can be introduced to the filter 110 when the fluid sample 124 is poured over or injected through the filter 110. The filter 110 can isolate or separate the infectious agent 102 or other molecules or cells from the supernatant of the fluid sample 124.

The filter housing 108 can have at least one opening which allows fluid or supernatant from the fluid sample 124 to evacuate the filter housing 108. For example, step 1A can include the additional step of discarding the fluid or supernatant from the fluid sample 124 through the opening after isolating the infectious agent 102 on the filter surface 126.

One advantage of the methods and systems 100 disclosed herein is the separation of any suspected or potential infectious agents 102 from the sensing device 116, the parameter analyzer 114, or a combination thereof. For example, the filter 110, the filter surface 126, the filter housing 108, or a combination thereof can prevent any suspected or potential infectious agents 102 from contacting any portion of the sensing device 116, the parameter analyzer 114, or a combination thereof. The filter 110, the filter surface 126, the filter housing 108, or a combination thereof can trap or isolate any suspected or potential infectious agents 102 on the filter surface 126 or in the filter housing 108.

In an alternative embodiment not shown in FIG. 1, a stimulus solution can be added to the fluid sample 124 before introducing the fluid sample 124 to the filter 110. The stimulus solution can be a nutrient or growth solution. The stimulus solution can be a super nutrient solution.

The fluid sample 124 can also be pre-filtered in a step before step 1A. This pre-filtering step can involve filtering the fluid sample 124 using an additional filter, a microfluidic filter, or a combination thereof to filter out other larger cellular components including blood cells or epithelial cells from the fluid sample 124 when the fluid sample 124 is composed of bodily fluid.

The same fluid delivery device 106 or another fluid delivery device 106 can also be used to deliver or inject a nutrient solution 130 to the filter housing 108 in step 1B. The fluid delivery device 106 can continuously or periodically expose the filter surface 126 to the nutrient solution 130.

After exposing the filter 110 to the nutrient solution 130, the filter 110 can be heated to a temperature of between 30° C. and 40° C. and allowed to incubate for an incubation period 132 in step 1C. In one embodiment, the filter 110 can be incubated while in the filter housing 108. In another embodiment, the filter 110 can be removed from the filter housing 108 prior to incubation. In some embodiments, the filter 110 can be incubated with the nutrient solution 130. In some embodiments, the incubation period 132 can range from 15 minutes to over one hour. In other embodiments, the incubation period 132 can be less than 15 minutes. The incubation period 132 can be adjusted based on the type of infectious agent 102 suspected in the fluid sample 124, such as the type of bacteria, fungus, virus, or prion.

The incubation period 132 can also be adjusted based on the suspected amount of the infectious agent 102 present in the fluid sample 124, the amount or volume of the fluid sample 124, or a combination thereof. For example, the incubation period 132 can be increased when the suspected amount of the infectious agent 102 or the volume of the fluid sample 124 is below a threshold amount. The filter 110 can be allowed to incubate with the nutrient solution 130 in order to promote the proliferation of the suspected infectious agent 102 on the filter surface 126. One advantage of incubating the filter 110 is to increase the sensitivity of the system 100 to small amounts of the suspected infectious agent 102. For example, incubating the filter 110 can allow the system 100 to reduce its level of detection.

After incubating the filter 110, the effluent or outflow of the nutrient solution 130 exposed to the filter 110 can be sampled. The effluent or outflow of the nutrient solution 130 exposed to the filter 110 can be referred to as the sample effluent 134.

In an alternative embodiment not shown in FIG. 1 but contemplated by this disclosure, the infectious agent 102 can be removed from the filter housing 108 by centrifugation or by filtration. For example, the infectious agent 102 can be removed from the filter housing 108 using another filter such as a syringe filter. The sample effluent 134 or supernatant after this filtration step can be collected and the solution characteristic of this sample effluent 134 can be analyzed.

The sample effluent 134 can be analyzed by a sensing device 116. In one embodiment, the sample effluent 134 can be analyzed by applying or introducing an aliquot of the sample effluent 134 to the sensing device 116 in step 1D(a). In another embodiment, the sample effluent 134 can be analyzed by inserting a portion of the sensing device 116 directly into the sample effluent 134 in step 1D(b).

The sample effluent 134 can comprise a solution characteristic. The solution characteristic can refer to one or more attributes of the solution making up the sample effluent 134. For example, the solution characteristic can include a concentration of a solute, an absolute number or molecular count of solutes in solution, a solution temperature, or a combination thereof. For example, the solution characteristic can refer to the amount or concentration of ions, organic molecules such as amino acids, vitamins or glucose, minerals, or other inorganic compounds in the sample effluent 134.

The solution characteristic can vary as a result of changes due to the energy use, growth, and metabolism of an infectious agent 102 in the fluid sample 124. For example, the solution characteristic can be a direct or indirect byproduct of a cellular activity undertaken by the infectious agent 102 such as cell metabolism or cell growth. The solution characteristic can vary as a result of ions, organic molecules, or minerals produced by, consumed by, or otherwise attributed to the infectious agent 102. For example, the solution characteristic can change as a result of an amount or concentration of nutrients in solution consumed or depleted by the infectious agent 102.

In one embodiment, the sample effluent 134 can comprise hydrogen ions ($H^+$) as a byproduct of bacterial cell metabolism or growth. In other embodiments, the sample effluent 134 can comprise adenosine triphosphate (ATP), carbon dioxide ($CO_2$), lactic acid, carbonic acid, nitrates ($NO_3^-$), or a combination thereof produced by or attributed to an infectious agent 102.

A change in the solution characteristic can cause a change in the electrical characteristic of the sensing device 116. The parameter analyzer 114 can detect a change in the electrical characteristic (see FIG. 4) of the sensing device 116 exposed to the sample effluent 134. In one embodiment, the parameter analyzer 114 can be a voltage meter. In other embodiments, the parameter analyzer 114 can be, but is not limited to, a multimeter, a source meter, an ammeter, a capacitance analyzer, or a combination thereof.

The electrical characteristic can include, but is not limited to, a voltage, an impedance, a current, a capacitance, a resistance, a resonant frequency, a noise level, a level of induction, or a combination thereof measured at or near the sensing device 116. The change in the electrical characteristic can include, but is not limited to, a voltage change, an impedance change, a current change, a capacitance change, a resistance change, a change in resonant frequency, a noise level change, an induction change, or a combination thereof measured at or near the sensing device 116.

As shown in FIG. 1, the parameter analyzer 114 can be fabricated on the same substrate 112 as the sensing device 116. In other embodiments, the parameter analyzer 114 can be a standalone unit or meter coupled to the sensing device 116. The parameter analyzer 114 can also be connected to or communicatively coupled to a display 113 or display component configured to provide a result of the detection or a read-out of the electrical characteristic of the sensing device 116. In certain embodiments, the parameter analyzer 114 can be a mobile device, a handheld device, a tablet device, or a computing device such as a laptop or desktop computer and the display 113 can be a mobile device display, a handheld device display, a tablet display, or a laptop or desktop monitor.

In one embodiment, the parameter analyzer 114 can display a result indicating the presence of an infectious agent 102 in the fluid sample 124 via the display 113 of the parameter analyzer 114. In another embodiment, the parameter analyzer 114 can wirelessly communicate a result indicating the presence of an infectious agent 102 in the fluid sample 124 to a computing device having the display 113.

The parameter analyzer 114, a reader, or a combination thereof can detect a change in the electrical characteristic of the sensing device 116 exposed to the sample effluent 134 corresponding to the presence of the infectious agent 102 in the fluid sample 124 introduced to the system 100 in step 1A.

The steps depicted in FIG. 1 do not require the particular order shown to achieve the desired result and certain steps or processes may occur in parallel.

Figure 2A:
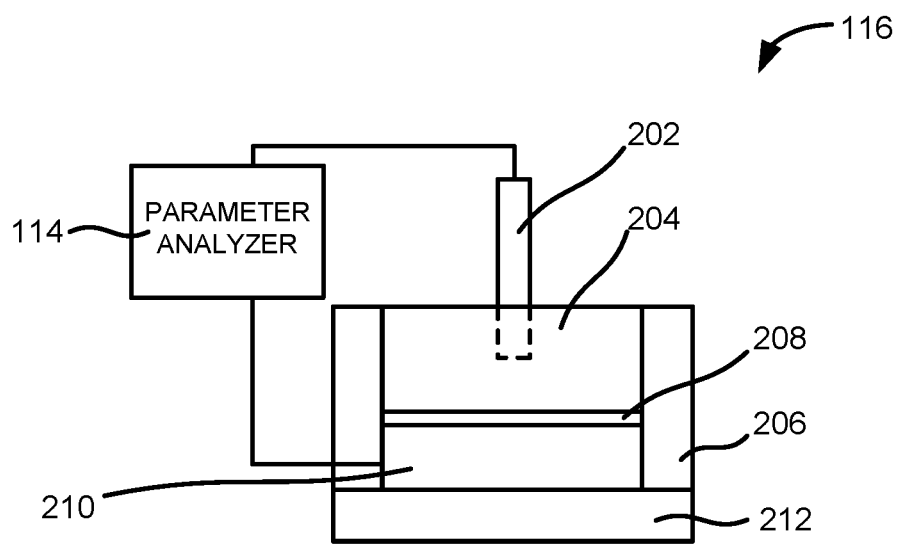
FIG. 2A illustrates a side view of an embodiment of an electrochemical cell having an external reference electrode.

FIG. 2A illustrates a side cross-sectional view of one embodiment of the sensing device 116. The sensing device 116 can be an electrochemical cell comprising an external reference electrode 202, an electrolyte 204 or electrically conducting solution retained by container walls 206, a functionalization layer 208, a conductor layer 210, and a substrate layer 212. The sensing device 116 can be connected or coupled to the parameter analyzer 114. The parameter analyzer 114 can be coupled to both the external reference electrode 202 and the conductor layer 210.

As shown in FIG. 2A, the external reference electrode 202 can extend into the electrolyte 204. In one embodiment, the electrolyte 204 can be the sample effluent 134. In other embodiments, the electrolyte 204 can comprise portions of the fluid sample 124.

The external reference electrode 202 can be used to apply a known potential to the electrolyte 204, which can be detected by the sensing device 116. The external reference electrode 202 can have a stable and well-known internal voltage and can act as a differential noise filter for removing electrical noise from measurements taken by the sensor. The system 100 can use the external reference electrode 202 to determine or record a relative change in the electrical characteristic of the sensing device 116 rather than having to ascertain an absolute change. The system 100 can also use the external reference electrode 202 to determine or record a relative difference between the electrical characteristics of multiple sensing devices 116. In one embodiment, the external reference electrode 202 can be a standalone probe or electrode. In other embodiments, the external reference electrode 202 can be coupled to the parameter analyzer 114 or a reader connected to the parameter analyzer 114. The parameter analyzer 114 can also be used to apply a voltage to the external reference electrode 202.

In one embodiment, the external reference electrode 202 can be a silver/silver chloride (Ag/AgCl) electrode. In other embodiments, the external reference electrode 202 can be, but is not limited to, a saturated calomel reference electrode (SCE) or a copper-copper (II) sulfate electrode (CSE). Since metals or other materials used to fabricate such external reference electrodes can often have an inhibitory or harmful effect on the infectious agents 102 under investigation, one advantage of the methods, devices, and systems 100 disclosed herein is the separation of the infectious agent 102 from the components of the system 100 in physical or fluid contact with these external reference electrodes.

The substrate layer 210 can be composed of, but is not limited to, any non-conducting material such as a polymer, an oxide, a ceramic, or a composite thereof. As depicted in FIG. 2A, the conductor layer 210 can be disposed on or cover the substrate layer 212.

The conductor layer 210 can be composed of, but is not limited to, a metal, a semiconducting material, a metal/metal-salt, or a combination thereof. For example, the conductor layer 210 can be composed of, but is not limited to, silicon, gold, silver, aluminum, platinum, or a composite thereof. The conductor layer 210 can also be an organic semiconductor, a carbon nanotube, graphene, an organic conductor such as those derived from polyacetylene, polyaniline, Quinacridone, Poly(3,4-ethylenedioxythiophene) or PEDOT, PEDOT: polystyrene sulfonate (PSS), or a combination thereof. The conductor layer 210 can be composed of any conducting material which allows an electrical property change to be measured, including, but is not limited to, a voltage change and/or a current change measured through the conductor layer 210, the functionalization layer 208, and the electrolyte 204 to the external reference electrode 202.

As depicted in FIG. 2A, the functionalization layer 208 can be disposed on or cover the conductor layer 210. The functionalization layer 208 can comprise silanes, DNA, proteins, antibodies, self-assembled mono layers (SAMs), oxides, buffered hydrogels, PVC, parylene, polyACE, or any other biochemically active materials. The functionalization layer 208 can be configured to facilitate the sensing device 116 from interacting with ions, analytes, or other molecules or byproducts in the electrolyte 204. For example, the functionalization layer 208 can be a pH-sensitive layer.

In one example, the functionalization layer 208 can comprise hydroxyl groups which can interact with hydrogen ions ($H^+$) in the electrolyte 204. This interaction can generate a change in the electrical characteristic of the sensing device 116 detected by the parameter analyzer 114. In one embodiment, this interaction can create a measurable change in the electrical characteristic of the sensing device 116 at the interface between the electrolyte 204/functionalization layer 208 or the interface between the electrolyte 204/conductor layer 210.

For example, the parameter analyzer 114 can be a voltmeter and the voltmeter can detect a voltage change ($\Delta V$) at or near the functionalization layer 208 exposed to the electrolyte 204. The voltage change can be determined with respect to the external reference electrode 202 extending into or in contact with the electrolyte 204. In this embodiment, the functionalization layer 208 and the conductor layer 210 can be considered part of a working or active electrode of the system 100.

To obtain a dynamic sensor response, the sensing device 116 can also be operated, in some instances, in a constant voltage mode or constant capacitance mode in one or more embodiments. When the sensing device 116 is operated in a constant voltage mode, the voltage can be set a fixed value (e.g., a flat-band voltage) and the voltage shift ($\Delta V$) that results from the surface potential generated at the interface of the electrolyte 204/conductor layer 210 or the electrolyte 204/functionalization layer 208 can be directly recorded.

As depicted in FIG. 2A, the electrolyte 204, the functionalization layer 208, and the conductor layer 210 can be surrounded by a container wall 206. The container wall 206 can be made of an inert or non-conductive material. The container wall 206 can hold or retain the electrolyte 204 or be responsible for delivering or introducing the sample effluent 134 to the sensing device 116.

Figure 2B:
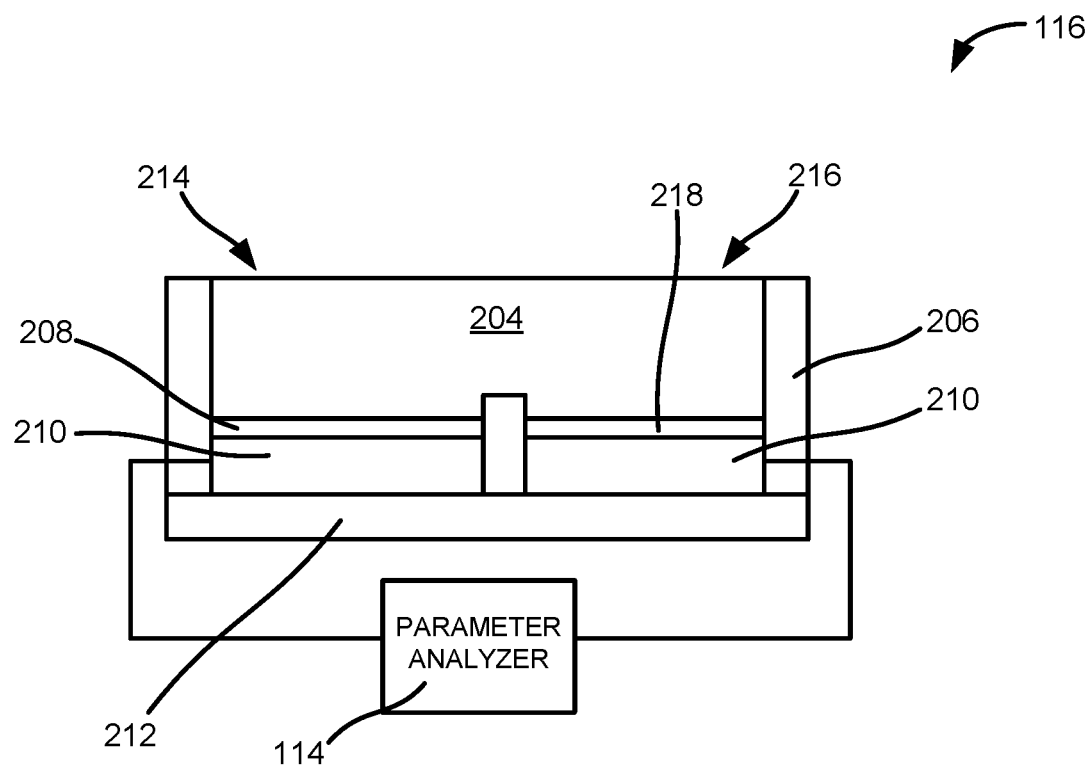
FIG. 2B illustrates a side view of an embodiment of an electrochemical cell having an on-chip reference electrode.

FIG. 2B illustrates a side cross-sectional view of another embodiment of the sensing device 116. In this embodiment, the sensing device 116 comprises a working electrode 214 and an on-chip reference electrode 216. In this embodiment, the working electrode 214 and the on-chip reference electrode 216 can be disposed on the same substrate layer 212. The substrate layer 212 can be composed of the same material as the substrate layer 212 depicted in FIG. 2A.

The electrolyte 204 can flow over or be exposed to both the working electrode 214 and the on-chip reference electrode 216 simultaneously. In this embodiment, the working electrode 214 and the on-chip reference electrode 216 can be separated by a container wall 214 or container divide.

The working electrode 214 can comprise the functionalization layer 208 disposed on or covering the conductor layer 210. The functionalization layer 218 can comprise silanes, DNA, proteins, antibodies, oxides, self-assembled mono layers (SAMs), buffered hydrogels, PVC, parylene, polyACE, or any other biochemically active materials.

As shown in FIG. 2B, a passivation layer 218 can be disposed on or cover the conductor layer 210. The passivation layer 218 can be configured to prevent the on-chip reference electrode 216 from interacting with analytes, ions, or other molecules or byproducts in the electrolyte 204. For example, the passivation layer 218 can be a pH-insensitive layer. The passivation layer 218 can comprise silanes, self-assembled monolayers (SAMs), buffered hydrogels, parylene, polyACE, or any other biochemically inert material.

In this embodiment, the parameter analyzer 114 can have a lead connection wire, such as a copper wire, connected to the conductor layer 210 of the working electrode 214 and another lead connection wire connected to the conductor layer 210 of the on-chip reference electrode 216.

In this and other embodiments, the sensing device 116 shown in FIG. 2B miniaturizes the sensor set-up shown in FIG. 2A. The on-chip reference electrode 216 obviates the need for an external reference electrode, such as the external reference electrode 202. The passivation layer 218 of the on-chip reference electrode 216 prevents the conductor layer 210 covered by the passivation layer 218 from interacting with the ions, analytes, or other molecules or byproducts in the electrolyte 204. This allows a reader or another device from being able to differentiate the electrical signals obtained by the parameter analyzer 114.

In one embodiment, the conductor layer 210 can be a metal covered with a metal salt such as a metal chloride. For example, the conductor layer 210 can be a silver/silver chloride contact. In this embodiment, the conductor layer 210 can be covered by a passivation layer 218 such as a KCL electrolyte gel, to prevent the conductor layer 210 from interacting with analytes, ions, or other molecules or byproducts in the electrolyte 204 and to act as a reference electrode.

Since metals or other materials used to fabricate such on-chip reference electrodes 216 can often have an inhibitory or harmful effect on the infectious agents 102 under investigation, one advantage of the methods, devices, and systems 100 disclosed herein is the separation of the infectious agent 102 from the components of the system 100 in physical or fluid contact with these on-chip reference electrodes 216.

Figure 3A:
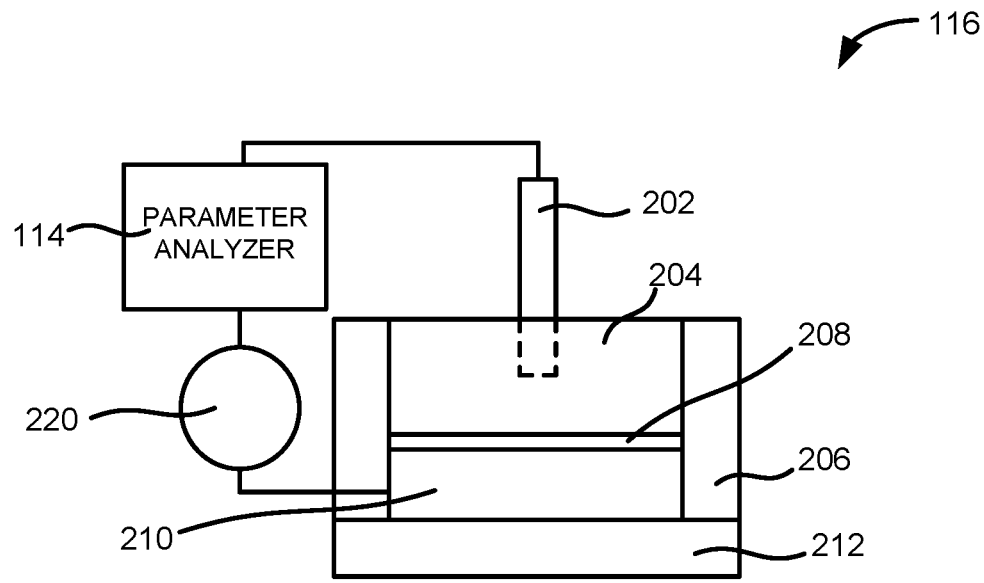
FIG. 3A illustrates a side view of an embodiment of an electrochemical cell having an external reference electrode and a power source.

FIG. 3A illustrates a side cross-sectional view of an embodiment of the sensing device 116 of FIG. 2A having a power source 220. The power source 220 can apply a DC or AC voltage (usually in the range of +/−5V) to the conductor layer 210 and the external reference electrode via the functionalization layer 208 and the electrolyte 204. This voltage can also be set to be used as a working point.

Depending on the concentration or amount of analytes, ions, molecules, or cellular byproducts present in the electrolyte 202, a change in the electrical characteristic (e.g., a horizontal shift ($\Delta V$) of the voltage measurement curve) will occur as the analytes, ions, molecules, or cellular byproducts interact with the sensing device 116. This change can be measured by the parameter analyzer 114. In one embodiment, when a voltage is applied over time or when different electrolyte 202 solutions are introduced to the sensing device 116, the analytes, ions, molecules, or cellular byproducts can interact with the functionalization layer 208, causing an additional electrical characteristic change, which can also be detected by the parameter analyzer 114.

Figure 3B:
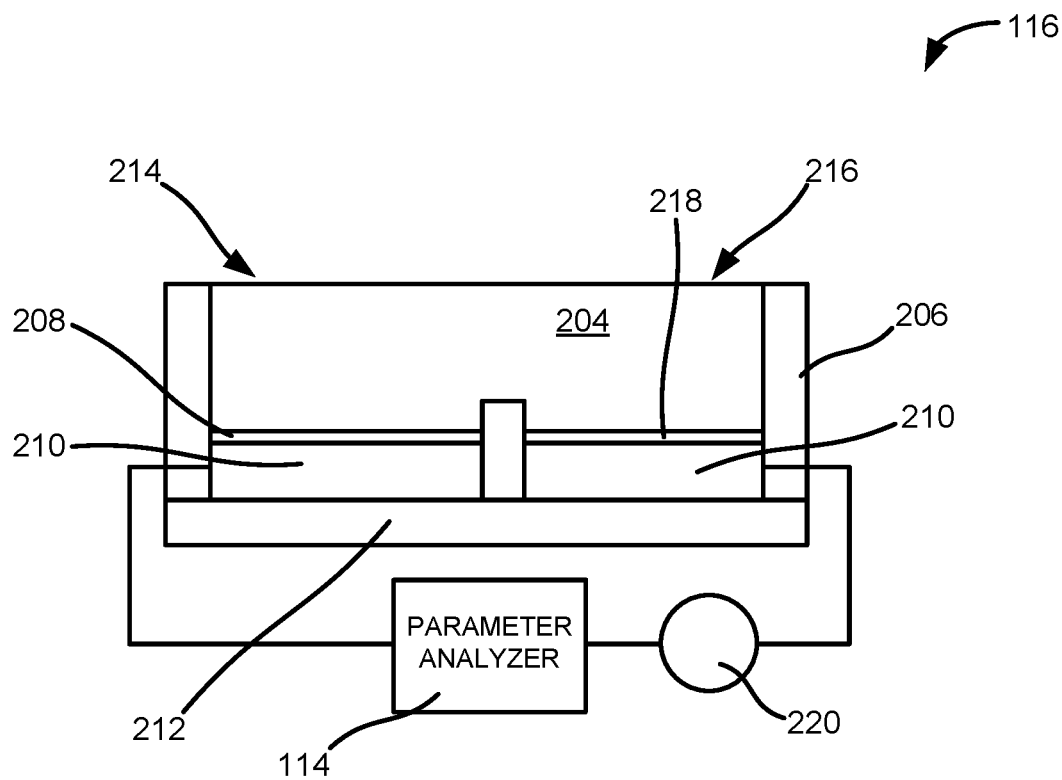
FIG. 3B illustrates a side view of an embodiment of an electrochemical cell having an on-chip reference electrode and a power source.

FIG. 3B illustrates a side cross-sectional view of an embodiment of the sensing device 116 of FIG. 2B having a power source 220. The power source 220 can apply a DC or AC voltage (usually in the range of +/−5V) between the conductor layer 210 of the working electrode 214, through the electrolyte 202 and the conductor layer 210 of the on-chip reference electrode 216. This setup can be a miniaturized form of the sensing device 116 of FIG. 3A. This voltage can also be set to be used as a working point. Depending on the concentration or amount of analytes, ions, molecules, or cellular byproducts present in the electrolyte 202, a change in the electrical characteristic, e.g. a horizontal shift ($\Delta V$) of the voltage measurement curve, can occur, as the analytes, ions, molecules, or cellular byproducts interact with the sensing device 116. This change can be measured by the parameter analyzer 114. In one configuration, when a voltage is applied over time or when different electrolytes 202 are introduced to the sensing device 116, the analytes, ions, molecules, or cellular byproducts can interact with the functionalization layer 208, causing an additional electrical characteristic change that can be detected by the parameter analyzer 114.

In another embodiment, a potential can be applied between the working electrode 214 through the electrolyte 204 to the on-chip reference electrode 216. The parameter analyzer 114 can then record a current, which flows between the two electrodes. Depending on the concentration or amount of analytes, ions, chemicals, molecules, or cellular byproducts present in the electrolyte 202, a change of the electrical characteristics (in this case, a shifting of the current measurement curve (ΔI)) can occur, as the analytes, ions, molecules, or cellular byproducts interact with the electrolyte 202 or the sensing device 116.

Figure 4:
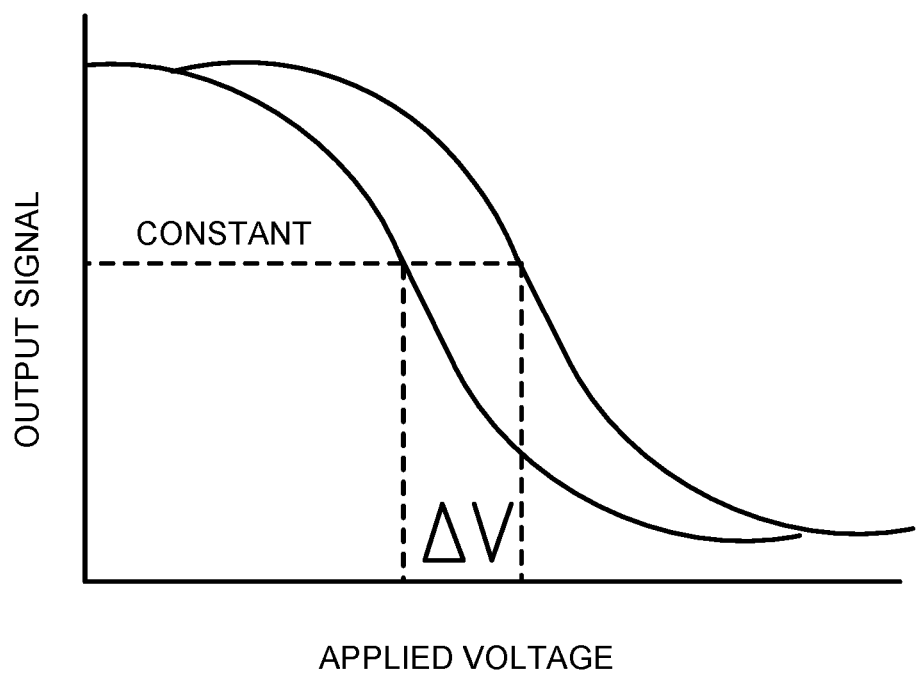
FIG. 4 illustrates an example readout from an analyzer or reader connected or communicatively coupled to the electrochemical cell.

FIG. 4 illustrates one example of an output/voltage curve generated based on readings obtained from the parameter analyzer 114. As can be seen in the output/voltage curve, the difference between the solution characteristics of two electrolyte 204 solutions or the electrolyte 204 solution over time can be measured by the change in the voltage (ΔV). In one embodiment, the output can be obtained when a constant voltage is applied to the system. The electrical output can include, but is not limited to, a current, a voltage, an impedance, a capacitance, and a resistance. In one example, the hydroxyl groups of functionalization layer 208 can interact with the hydrogen ions ($H^+$) in the electrolyte 204. This can create an additional voltage/potential or capacitance at, for example, the interface between the functionalization layer 208 and the electrolyte 204 or the conductor layer 210 and the electrolyte 204. This additional voltage will alter the output/voltage curve or the overall electrical characteristic of the sensing device 116. To obtain a dynamic sensor response, the sensing device 116 can also be operated in a constant output mode. In this constant output mode, the electrical output, such as a voltage or current, can be set at a fixed value (e.g., a flat-band current or voltage) and the voltage shift (ΔV) that results from the surface potential generated at the interface of the electrolyte 204 and functionalization layer 208 can be directly recorded.

Figure 5:
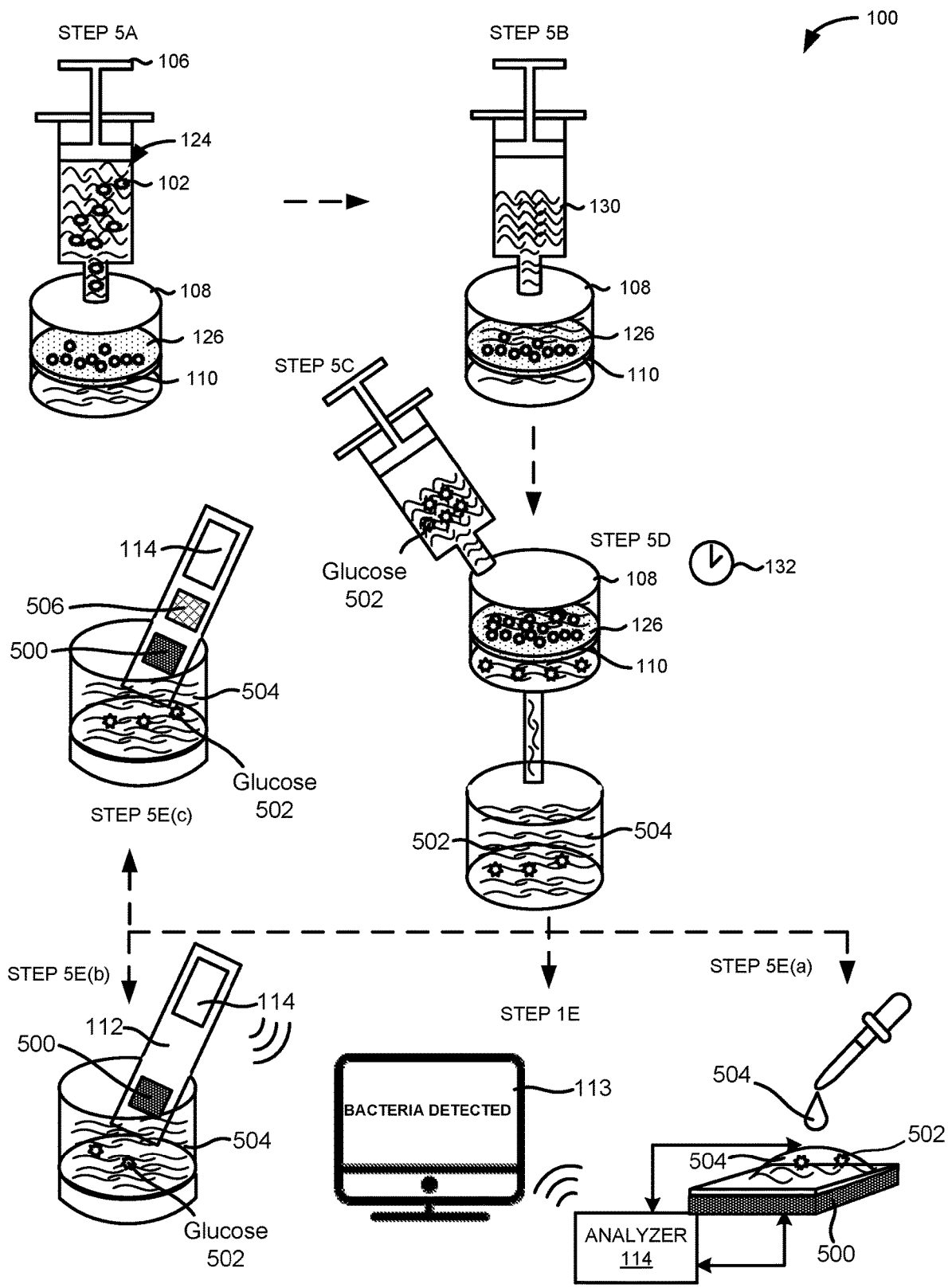
FIG. 5 illustrates another embodiment of a system for detecting infectious agents in a fluid sample.

FIG. 5 illustrates another embodiment of a system 100 for detecting an infectious agent 102 in a fluid sample 124. In one embodiment, the system 100 can comprise the fluid delivery device 106, the filter housing 108 containing the filter 110, a sensing device 500, and the parameter analyzer 114.

As shown in FIG. 5, the parameter analyzer 114 can be integrated into one device with the sensing device 500. For example, the parameter analyzer 114 can be fabricated on the same substrate 112 as the sensing device 500. In other embodiments, the parameter analyzer 114 can be a stand-alone unit or device coupled to the sensing device 500.

As illustrated in FIG. 5, the fluid delivery device 106 can deliver or inject the fluid sample 124 into the filter housing 108 in step 5A. The fluid delivery device 106, the filter housing 108, the filter 110, and the filter surface 126 can be the same fluid delivery device 106, the same filter housing 108, the same filter 110, and the same filter surface 126, respectively, depicted in FIG. 1.

The filter housing 108 can have at least one opening which allows fluid or supernatant from the fluid sample 124 to evacuate the filter housing 108. For example, step 5A can include the additional step of discarding the fluid or supernatant from the fluid sample 124 through the opening after isolating the infectious agent 102 on the filter surface 126.

One advantage of the methods and systems 100 disclosed herein is the separation of any suspected or potential infectious agents 102 from the sensing device 500, the parameter analyzer 114, or a combination thereof. For example, the filter 110, the filter surface 126, the filter housing 108, or a combination thereof can prevent any suspected or potential infectious agents 102 from contacting any portion of the sensing device 500, the parameter analyzer 114, or a combination thereof.

In an alternative embodiment not shown in FIG. 5, a stimulus solution can be added to the fluid sample 124 before introducing the fluid sample 124 to the filter 110. The stimulus solution can be a nutrient or growth solution. The stimulus solution can be a super nutrient solution.

The fluid sample 124 can also be pre-filtered in a step before step 5A. This pre-filtering step can involve filtering the fluid sample 124 using an additional filter, a microfluidic filter, or a combination thereof to filter out other larger cellular components including blood cells or epithelial cells from the fluid sample 124 when the fluid sample 124 is composed of bodily fluid.

The same fluid delivery device 106 or another fluid delivery device 106 can also be used to deliver or inject a nutrient solution 130 to the filter housing 108 in step 5B. The fluid delivery device 106 can continuously or periodically expose the filter surface 126 to the nutrient solution 130.

After exposing the filter 110 to the nutrient solution 130, another fluid delivery device 106 can be used to deliver or inject a known concentration of glucose 502 to the filter housing 108 or the filter 110 in step 5C. For example, 20 mM or 360 mg/dl of glucose can be delivered or injected to the filter housing 108.

The filter housing 108 can be heated to a temperature of between 30° C. and 40° C. and allowed to incubate for an incubation period 132 in step 5D. In one embodiment, the filter 110 can be incubated while in the filter housing 108. In another embodiment, the filter 110 can be removed from the filter housing 108 prior to incubation. In some embodiments, the filter 110 can be incubated with the known concentration of glucose 502. In other embodiments, the filter 110 can be incubated with the known concentration of glucose 502 and the nutrient solution 130. In some embodiments, the incubation period 132 can range from one hour to five hours. In other embodiments, the incubation period 132 can be more than five hours. In further embodiments, the incubation period 132 can be less than one hour. The incubation period 132 can be adjusted based on the type of infectious agent 102 suspected in the fluid sample 124, such as the type of bacteria, fungus, virus, or prion.

The incubation period 132 can also be adjusted based on the suspected amount of the infectious agent 102 present in the fluid sample 124, the amount or volume of the fluid sample 124, the amount of glucose 502 added, or a combination thereof. For example, the incubation period 132 can be increased when the suspected amount of the infectious agent 102 or the volume of the fluid sample 124 is below a threshold amount. The filter 110 can be allowed to incubate with the nutrient solution 130 in order to promote the proliferation of the suspected infectious agent 102 on the filter surface 126.

One advantage of incubating the filter 110 is to increase the sensitivity of the system 100 to small amounts of the suspected infectious agent 102. For example, incubating the filter 110 can allow the system 100 to reduce its level of detection.

After incubating the filter 110, the effluent or outflow of the nutrient solution 130 and/or the solution of glucose 502 exposed to the filter 110 can be sampled. The effluent or outflow of the nutrient solution 130 and/or the solution of glucose 502 exposed to the filter 110 can be referred to as the sample effluent 504.

The sample effluent 504 can be analyzed by the sensing device 500. In the example embodiment shown in FIG. 5, the sensing device 500 can be a glucose sensor. The glucose sensor will be discussed in more detail below.

In one embodiment, the sample effluent 504 can be analyzed by applying or introducing an aliquot of the sample effluent 504 to the sensing device 500 in step 5E(a). In another embodiment, the sample effluent 504 can be analyzed by inserting a portion of the sensing device 500 directly into the sample effluent 504 in step 5E(b). In yet another embodiment, the sample effluent 504 can be analyzed by inserting a sensing device 500 having both a glucose sensor and another sensor 506 directly into the sample effluent 504 in step 5E(c). The other sensor 506 can include the sensing device 116 such as the electrochemical cell of FIG. 2A, 2B, 3A or 3B or a light-addressable potentiometric (LAP) sensor.

In an alternative embodiment not shown in FIG. 5 but contemplated by this disclosure, the infectious agent 102 can be removed from the filter housing 108 by centrifugation or by filtration. For example, the infectious agent 102 can be removed from the filter housing 108 using a filter such as a syringe filter. The sample effluent 504 or supernatant after this filtration step can be collected and the solution characteristic, including the glucose concentration, of this sample effluent 504 can be analyzed by a glucose sensor serving as the sensing device 500. In all such embodiments, the infectious agent 102 is separated from the sample effluent 504 under analysis.

In one embodiment, the glucose sensor and the other sensor 506 can be fabricated on the same substrate 112 or test-strip. In this and other embodiments, the glucose sensor can be one component of a multisensory having the other sensor 506 as another component.

The sample effluent 504 can comprise a solution characteristic. The solution characteristic can refer to one or more attributes of the solution making up the sample effluent 504. In some embodiments, the solution characteristic can include a concentration of glucose, an absolute number or molecular count of glucose, or a combination thereof. In other embodiments, the solution characteristic can include a concentration of a byproduct of glucose metabolism or glucose production, an absolute number or molecular count of such a byproduct, a solution temperature, or a combination thereof. For example, the solution characteristic can change as a result of a change in the known concentration of the glucose solution 502 added to the system 100 in step 5C.

The solution characteristic can vary as a result of changes due to the energy use, growth, and metabolism of the infectious agent 102 isolated or trapped by the filter 110. For example, the solution characteristic can be a direct or indirect byproduct of a cellular activity undertaken by the infectious agent 102 such as cell metabolism or cell growth. The solution characteristic can vary as a result of glucose or other molecules or ions produced or consumed by the infectious agent 102 on the filter surface 126.

A change in the solution characteristic can cause a change in the electrical characteristic of the sensing device 500. The parameter analyzer 114 can detect a change in an electrical characteristic (see FIG. 7) of the sensing device 500 exposed to the sample effluent 504. The parameter analyzer 114 can be, but is not limited to, a voltmeter, a multimeter, an ammeter, a capacitance analyzer, or a combination thereof.

The electrical characteristic can include, but is not limited to, a voltage, an impedance, a current, a capacitance, a resistance, a resonant frequency, a noise level, a level of induction, or a combination thereof measured at or near the sensing device 500. The change in the electrical characteristic can include, but is not limited to, a voltage change, an impedance change, a current change, a capacitance change, a resistance change, a change in resonant frequency, a noise level change, an induction change, or a combination thereof measured at or near the sensing device 500.

As shown in FIG. 5, the parameter analyzer 114 can be fabricated on the same substrate 112 as the sensing device 500. In other embodiments, the parameter analyzer 114 can be a standalone unit or meter coupled to the sensing device 500. The parameter analyzer 114 can also be connected to or communicatively coupled to the display 113 or display component configured to provide a result of the detection or a read-out of the electrical characteristic of the sensing device 500. In certain embodiments, the parameter analyzer 114 can be a mobile device, a handheld device, a tablet device, or a computing device such as a laptop or desktop computer and the display 113 can be a mobile device display, a handheld device display, a tablet display, or a laptop or desktop monitor.

In one embodiment, the parameter analyzer 114 can display a result indicating the presence of an infectious agent 102 in the fluid sample 124 via the display 113 of the parameter analyzer 114. In another embodiment, the parameter analyzer 114 can wirelessly communicate a result indicating the presence of an infectious agent 102 in the fluid sample 124 to a computing device having the display 113.

The parameter analyzer 114, a reader, or a combination thereof can detect a change in the electrical characteristic of the sensing device 500 exposed to the sample effluent 504 corresponding to the presence of the infectious agent 102 in the system 100. The steps depicted in FIG. 5 do not require the particular order shown to achieve the desired result and certain steps or processes may occur in parallel.

Figure 6A:
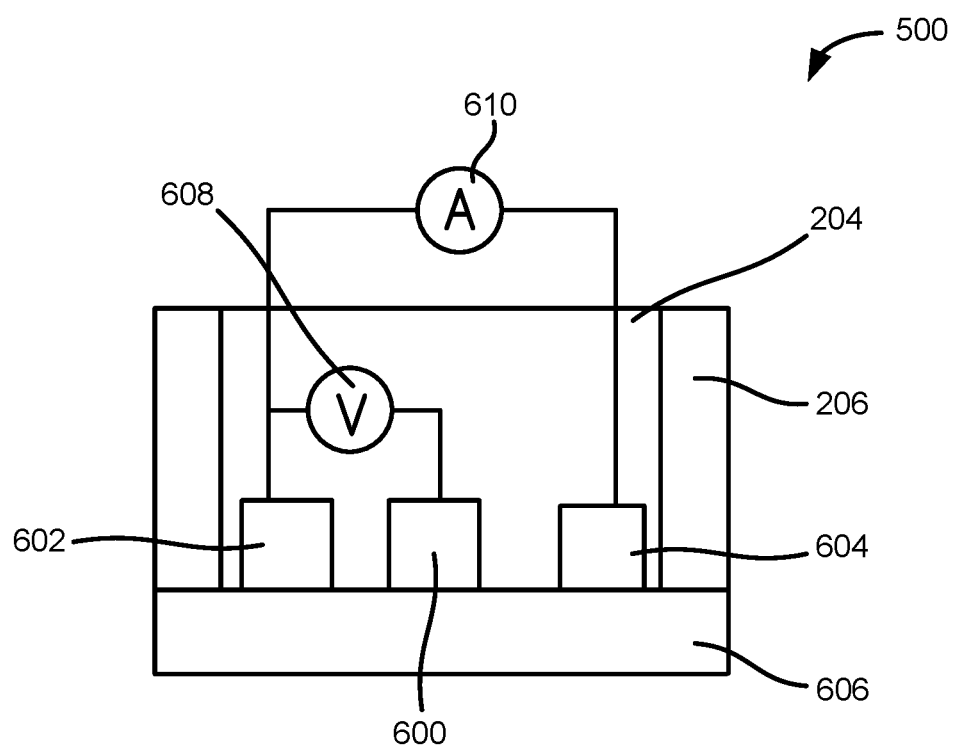
FIG. 6A illustrates a side view of an embodiment of an electrochemical sensor of the system.

FIG. 6A illustrates a side cross-sectional view of an embodiment of the sensing device 500. In one embodiment, the sensing device 500 can be an electrochemical sensing device (e.g., a glucose sensing device). In this embodiment, the sensing device 500 comprises a working electrode 600, a reference electrode 602, and a counter electrode 604. The working electrode 600, the reference electrode 602, and the counter electrode 604 can be disposed on the same substrate layer 606. The substrate layer 606 can be composed of, but is not limited to, any non-conducting material such as a polymer, an oxide, a ceramic, or a composite thereof. For example, the substrate layer 606 can be composed of the same material as the substrate layer 212 depicted in FIG. 2A.

The electrolyte 204 can flow over or be exposed to the working electrode 600, the reference electrode 602, and the counter electrode 604 simultaneously. As depicted in FIG. 6, the electrolyte 204 can be surrounded by the container wall 206. The container wall 206 can be made of an inert or non-conductive material. The container wall 206 can hold or retain the electrolyte 204 or be responsible for delivering or introducing the sample effluent 504 to the sensing device 500.

The sensing device 500 can be connected to a voltmeter 608 and an ammeter 610 or any other meter or measurement device. The voltmeter 608 can have one lead connection wire, such as a copper wire, connected to the working electrode 600 and another lead connection wire connected to the reference electrode 602. The ammeter 610 can also have one lead connection wire connected to the reference electrode 602 and another lead connection wire connected to the counter electrode 604.

Figure 6B:
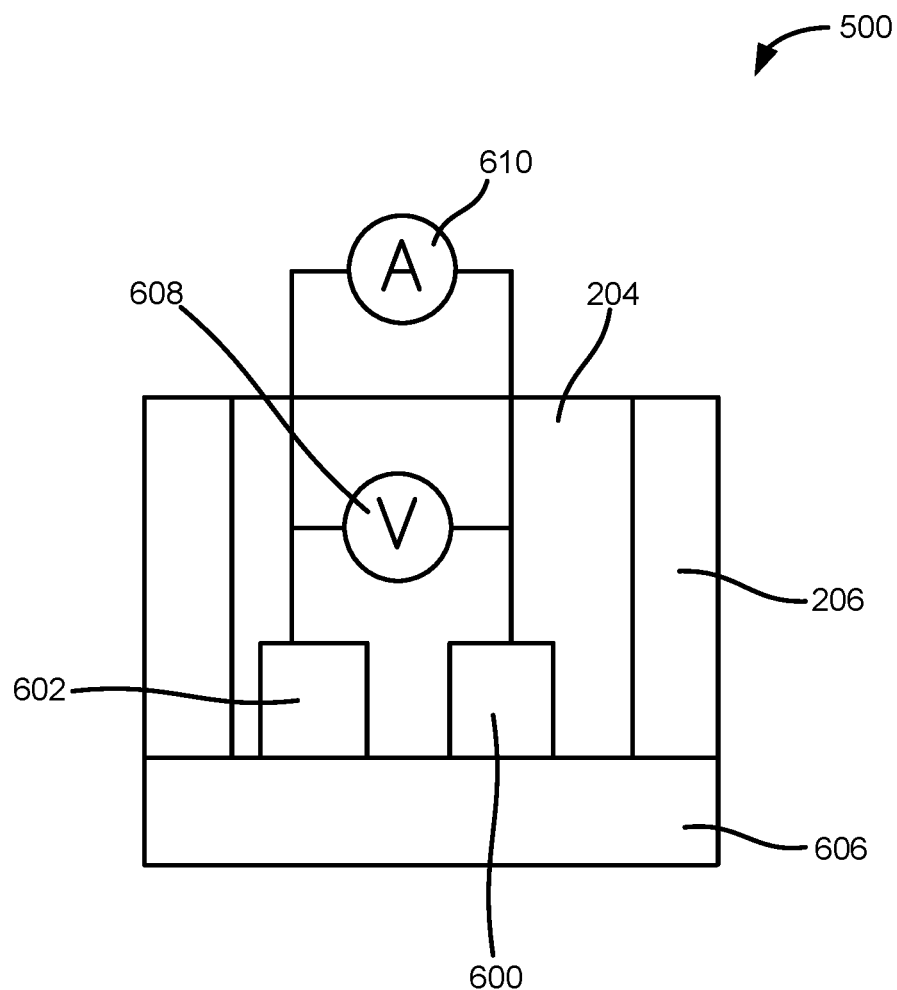
FIG. 6B illustrates a side view of another embodiment of an electrochemical sensor of the system.

FIG. 6B illustrates a side cross-sectional view of another embodiment of the sensing device 500. The sensing device 500 of FIG. 6B can be a two electrode setup where the reference electrode 602 can also act as a counter electrode. In this embodiment, a voltage can be applied between the reference electrode 602 and the working electrode 600. At the same time, the current flowing from the reference electrode 602 through the electrolyte 204 to the working electrode 600 can be measured. To detect a given analyte, molecule, ion, or DNA, a known chemical or solution can be added to the electrolyte 204. This chemical can react with the target analytes, ions, molecules or cellular byproducts, altering the current curve of FIG. 7. In one example embodiment, the oxidation of glucose to gluconolactone or gluconic acid (catalyzed, for example, by glucose oxidase) can be measured. In another reaction, glucose dehydrogenase can be used as an enzyme. Additional chemicals can also be added to generate an electrical current that can be measured by the system. The total charge passing through the electrodes can be proportional to the amount of glucose in the solution that has reacted with the enzyme.

Figure 7:
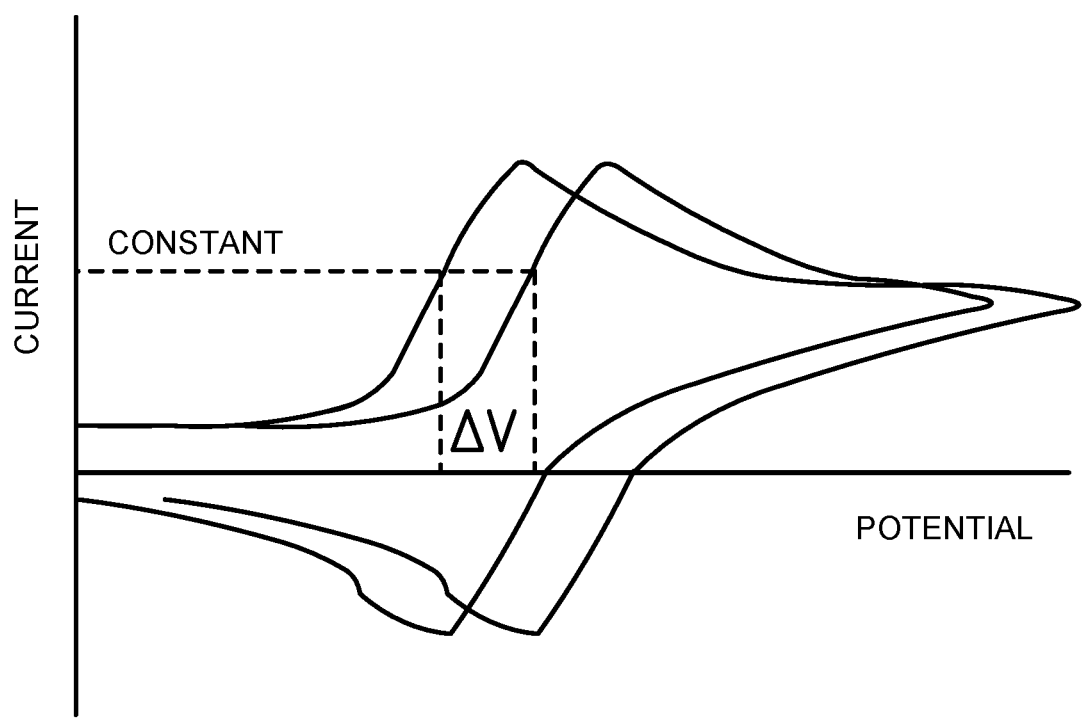
FIG. 7 illustrates an example readout from an analyzer or reader connected or communicatively coupled to the glucose sensor.

FIG. 7 illustrates one example of a current/voltage curve generated based on readings obtained from the voltmeter 609 and the ammeter 610 connected to the sensing device 500. As can be seen in the current/voltage curve, the difference between the solution characteristics of two electrolyte 204 solutions or the electrolyte 204 solution over time can be measured by the change in the voltage ($\Delta V$) at a constant current. To obtain a dynamic sensor response, the sensing device 500 can also be operated in a constant voltage mode. In this constant voltage mode, a fixed voltage can be applied between the electrodes and a current can be recorded. Different concentrations of the target analytes, ions, molecules, or cellular byproducts can result in different current outputs. In another embodiment, a current can be fixed between the two electrodes while the voltage is recorded. In this embodiment, the current change ($\Delta I$) can be measured over time at the fixed voltage.

Figure 8:
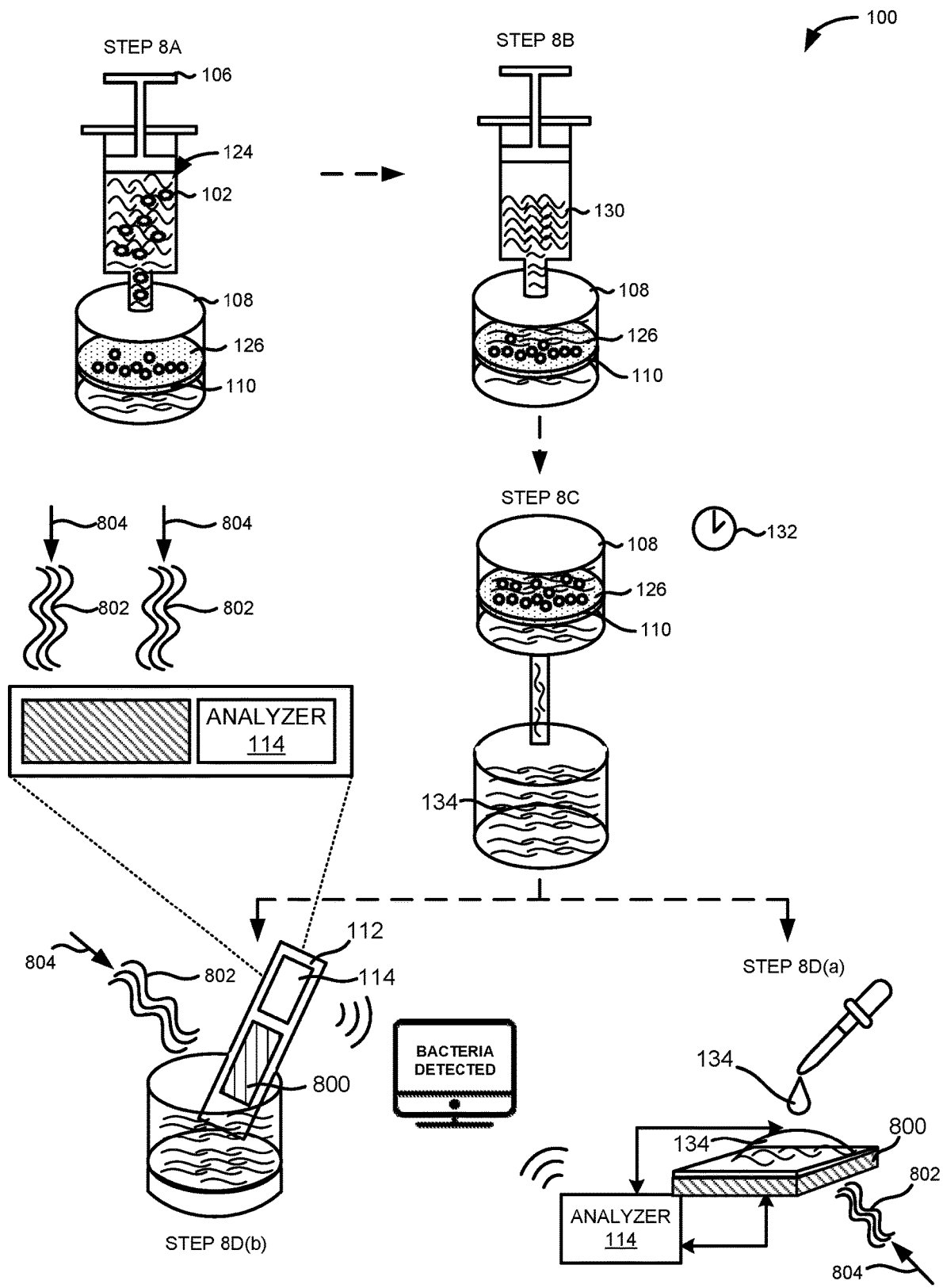
FIG. 8 illustrates yet another embodiment of a system for detecting infectious agents in a fluid sample.

FIG. 8 illustrates another embodiment of a system 100 for detecting an infectious agent 102 in a fluid sample 124. In one embodiment, the system 100 can comprise the fluid delivery device 106, the filter housing 108 containing the filter 110, a sensing device 800, and the parameter analyzer 114.

As shown in FIG. 8, the parameter analyzer 114 can be integrated into one device with the sensing device 800. For example, the parameter analyzer 114 can be fabricated on the same substrate 112 as the sensing device 800. In other embodiments, the parameter analyzer 114 can be a stand-alone unit or device coupled to the sensing device 800.

As illustrated in FIG. 8, the fluid delivery device 106 can deliver or inject the fluid sample 124 into the filter housing 108 in step 8A. The fluid delivery device 106, the filter housing 108, the filter 110, and the filter surface 126 can be the same fluid delivery device 106, the same filter housing 108, the same filter 110, and the same filter surface 126, respectively, depicted in FIG. 1.

The filter housing 108 can have at least one opening which allows fluid or supernatant from the fluid sample 124 to evacuate the filter housing 108. For example, step 8A can include the additional step of discarding the fluid or supernatant from the fluid sample 124 through the opening after isolating the infectious agent 102 on the filter surface 126.

One advantage of the methods and systems 100 disclosed herein is the separation of any suspected or potential infectious agents 102 from the sensing device 800, the parameter analyzer 114, or a combination thereof. For example, the filter 110, the filter surface 126, the filter housing 108, or a combination thereof can prevent any suspected or potential infectious agents 102 from contacting any portion of the sensing device 800, the parameter analyzer 114, or a combination thereof.

In an alternative embodiment not shown in FIG. 8, a stimulus solution can be added to the fluid sample 124 before introducing the fluid sample 124 to the filter 110. The stimulus solution can be a nutrient or growth solution. The stimulus solution can be a super nutrient solution.

The fluid sample 124 can also be pre-filtered in a step before step 8A. This pre-filtering step can involve filtering the fluid sample 124 using an additional filter, a microfluidic filter, or a combination thereof to filter out other larger cellular components including blood cells or epithelial cells from the fluid sample 124 when the fluid sample 124 is composed of bodily fluid.

The same fluid delivery device 106 or another fluid delivery device 106 can also be used to deliver or inject a nutrient solution 130 to the filter housing 108 in step 8B. The fluid delivery device 106 can continuously or periodically expose the filter surface 126 to the nutrient solution 130.

After exposing the filter 110 to the nutrient solution 130, the filter housing 108 can be heated to a temperature of between 30° C. and 40° C. and allowed to incubate for an incubation period 132 in step 8C. In one embodiment, the filter 110 can be incubated while in the filter housing 108. In another embodiment, the filter 110 can be removed from the filter housing 108 prior to incubation. In some embodiments, the filter 110 can be incubated with the nutrient solution 130. The incubation period 132 can range from 15 minutes to over one hour. In other embodiments, the incubation period 132 can be less than 15 minutes. The incubation period 132 can be adjusted based on the type of infectious agent 102 suspected in the fluid sample 124, such as the type of bacteria, fungus, virus, or prion.

The incubation period 132 can also be adjusted based on the suspected amount of the infectious agent 102 present in the fluid sample 124, the amount or volume of the fluid sample 124, or a combination thereof. For example, the incubation period 132 can be increased when the suspected amount of the infectious agent 102 or the volume of the fluid sample 124 is below a threshold amount. The filter 110 can be allowed to incubate with the nutrient solution 130 in order to promote the proliferation of the suspected infectious agent 102 on the filter surface 126. One advantage of incubating the filter 110 is to increase the sensitivity of the system 100 to small amounts of the suspected infectious agent 102. For example, incubating the filter 110 can allow the system 100 to reduce its level of detection.

After incubating the filter 110, the effluent or outflow of the nutrient solution 130 exposed to the filter 110 can be sampled. The effluent or outflow of the nutrient solution 130 exposed to the filter 110 can be referred to as the sample effluent 134.

In an alternative embodiment not shown in FIG. 8 but contemplated by this disclosure, the infectious agent 102 can be removed from the filter housing 108 by centrifugation or by filtration. For example, the infectious agent 102 can be removed from the filter housing 108 using another filter such as a syringe filter. The sample effluent 134 or supernatant after this filtration step can be collected and the solution characteristic of this sample effluent 134 can be analyzed.

The sample effluent 134 can be analyzed by the sensing device 800. In the example embodiment shown in FIG. 8, the sensing device 800 can be a light-addressable potentiometric (LAP) sensor. The LAP sensor will be discussed in more detail below.

In one embodiment, the sample effluent 134 can be analyzed by applying or introducing an aliquot of the sample effluent 134 to the sensing device 800 in step 8D(a). Step 8D(a) can also involve using a light source 804 to direct light 802 of a predetermined wavelength at the sensing device 800. The light source 804 can be a modulated light source. The light source 804 can be or include, but is not limited to, a focused laser beam, a light bulb, a light-emitting diode (LED), an organic LED (OLED), a liquid crystal display (LCD), or a combination thereof. In another embodiment, the sample effluent 134 can be analyzed by inserting a portion of the sensing device 800 directly into the sample effluent 134 in step 8D(b). Step 8D(b) can also involve using the light source 804 to direct light 802 of a predetermined wavelength at the sensing device 800.

The sample effluent 134 can comprise a solution characteristic. The solution characteristic can refer to one or more attributes of the solution making up the sample effluent 134. In some embodiments, the solution characteristic can include a concentration of an analyte, molecule, or ion, an absolute number or molecular count of an analyte, molecule, or ion, or a combination thereof. In other embodiments, the solution characteristic can include a solution temperature. The solution characteristic can vary as a result of changes due to the energy use, growth, and metabolism of the infectious agent 102 isolated or trapped by the filter 110. For example, the solution characteristic can be a direct or indirect byproduct of a cellular activity undertaken by the infectious agent 102 such as cell metabolism or cell growth. The solution characteristic can vary as a result of molecules or ions produced or consumed by the infectious agent 102.

A change in the solution characteristic can cause a change in the electrical characteristic of the sensing device 800. The parameter analyzer 114 can detect a change in an electrical characteristic (see FIG. 10) of the sensing device 800 exposed to the sample effluent 134. The parameter analyzer 114 can include, but is not limited to, any combination of a voltmeter, a multimeter, or an ammeter. For example, the parameter analyzer 114 in this embodiment can include the voltage source 908 and the ammeter 910 depicted in FIG. 9).

The electrical characteristic can include, but is not limited to, a voltage, a current, a photocurrent, or a combination thereof measured at or near the sensing device 800. The change in the electrical characteristic can include, but is not limited to, a voltage change, a current change, a photocurrent change, or a combination thereof measured at or near the sensing device 800.

As shown in FIG. 8, the parameter analyzer 114 can be fabricated on the same substrate 112 as the sensing device 800. In other embodiments, the parameter analyzer 114 can be a standalone unit or meter coupled to the sensing device 800. The parameter analyzer 114 can also be connected to or communicatively coupled to the display 113 or display component configured to provide a result of the detection or a read-out of the electrical characteristic of the sensing device 800. In certain embodiments, the parameter analyzer 114 can be a mobile device, a handheld device, a tablet device, or a computing device such as a laptop or desktop computer and the display 113 can be a mobile device display, a handheld device display, a tablet display, or a laptop or desktop monitor.

In one embodiment, the parameter analyzer 114 can display a result indicating the presence of an infectious agent 102 in the fluid sample 124 via the display 113 of the parameter analyzer 114. In another embodiment, the parameter analyzer 114 can wirelessly communicate a result indicating the presence of an infectious agent 102 in the fluid sample 124 to a computing device having the display 113.

The parameter analyzer 114, a reader, or a combination thereof can detect a change in the electrical characteristic of the sensing device 800 exposed to the sample effluent 134 corresponding to the presence of the infectious agent 102 in the system 100.

The steps depicted in FIG. 8 do not require the particular order shown to achieve the desired result and certain steps or processes may occur in parallel.

Figure 9:
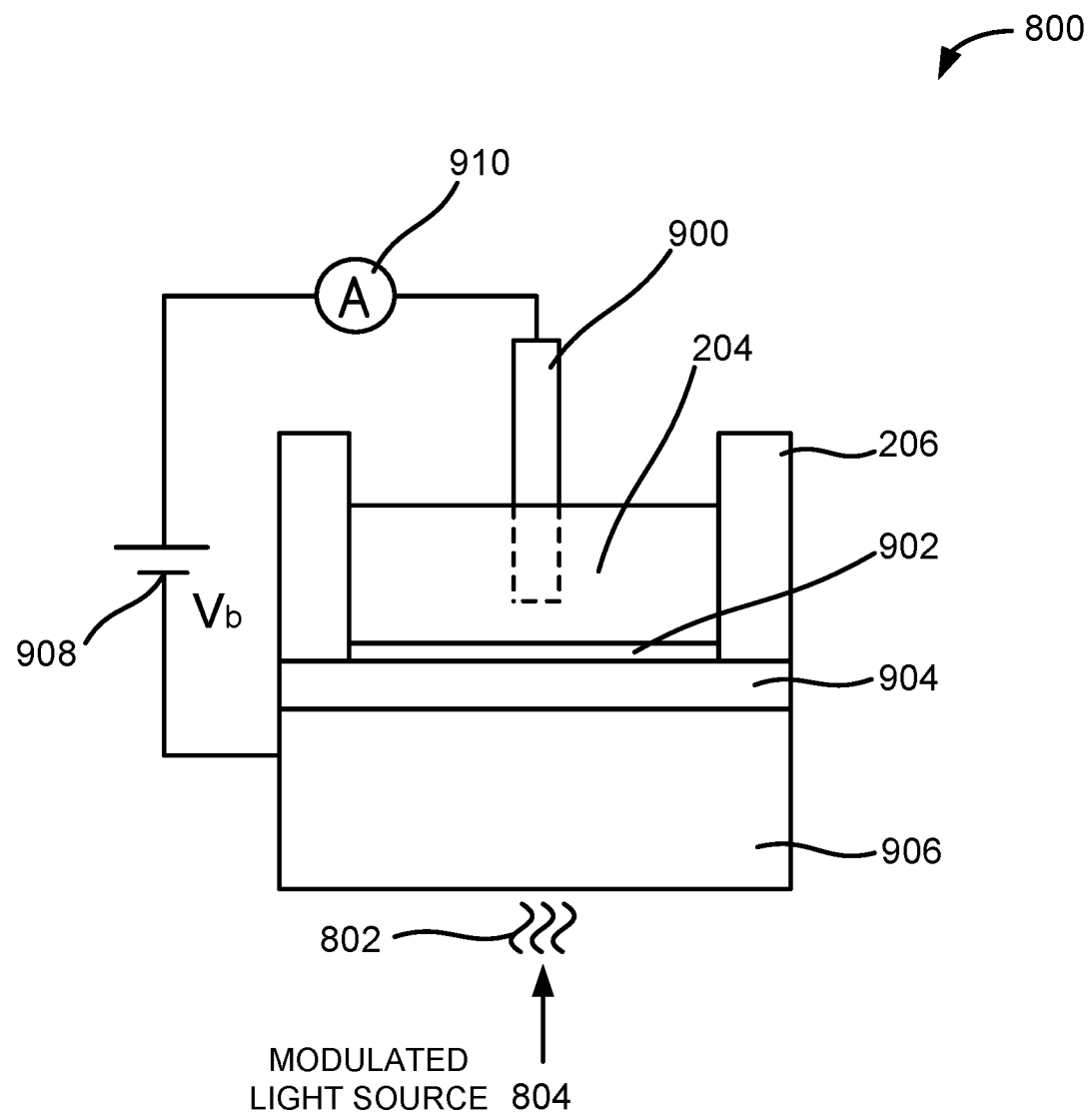
FIG. 9 illustrates a side view of an embodiment of a light-addressable potentiometric (LAP) sensor of the system.

FIG. 9 illustrates a side cross-sectional view of one embodiment of the sensing device 800. In one embodiment, the sensing device 800 can be a photocurrent sensor such as a light-addressable potentiometric (LAP) sensor. The sensing device 800 can comprise an external reference electrode 900, an electrolyte 204 or electrically conducting solution retained by container walls 206, a functionalization layer 902, an insulator layer 904, and a semiconductor layer 906. The sensing device 800 can be connected or coupled to a voltage source 908 and an ammeter 910. The voltage source 908 can be connected in series with the ammeter 910, for example, with one lead connection wire connected to the semiconductor layer 906 and the other lead connection wire connected to the external reference electrode 900.

As depicted in FIG. 9, the electrolyte 204 and the functionalization layer 902 can be surrounded by a container wall 206. The container wall 206 can be made of an inert or non-conductive material. The container wall 206 can hold or retain the electrolyte 204 or be responsible for delivering or introducing the sample effluent 134 to the sensing device 800.

As shown in FIG. 9, the external reference electrode 900 can extend into the electrolyte 204. In one embodiment, the electrolyte 204 can be the sample effluent 134. In other embodiments, the electrolyte 204 can comprise portions of the fluid sample 124.

The voltage source 908 can apply a known potential to the sensing device 800 through the external reference electrode 900. This voltage can be, but is not limited to, a DC or AC voltage. In one embodiment, the external reference electrode 900 can be a silver/silver chloride (Ag/AgCl) electrode. In other embodiments, the external reference electrode 202 can be a saturated calomel reference electrode (SCE) or a copper-copper (II) sulfate electrode (CSE).

Since metals or other materials used to fabricate such external reference electrodes can often have an inhibitory or harmful effect on the infectious agents 102 under investigation, one advantage of the methods, devices, and systems 100 disclosed herein is the separation of the infectious agent 102 from the components of the system 100 in physical or fluid contact with these external reference electrodes.

The sensing device 800 can comprise the insulator layer 904 disposed on or covering the semiconductor layer 906. The semiconductor layer 906 can be a layer of doped semiconducting material. The semiconductor layer 906 can be composed of, but is not limited to, a layer of doped silicon. The semiconductor layer 906 can also be made of an organic semiconductor, a carbon nanotube, graphene, an organic conductor such as those derived from polyacetylene, polyaniline, Quinacridone, Poly(3,4-ethylenedioxythiophene) or PEDOT, PEDOT: polystyrene sulfonate (PSS), or a combination thereof.

The insulator layer 904 (which can also be referred to as an isolator layer) can be a high-k dielectric layer or a material layer having a high dielectric constant (k). For example, the insulator layer 904 can comprise aluminum oxide, hafnium oxide, titanium oxide, zirconium oxide, yttrium oxide, tantalum oxide, hafnium silicate, zirconium silicate, silicon nitride, aluminum nitride, hafnium nitride, zirconium nitride, or a combination thereof. As a more specific example, the insulator layer 904 can comprise aluminum dioxide, hafnium dioxide, zirconium dioxide, or a combination thereof. In other embodiments, the insulator layer 216 can comprise a silicon dioxide layer.

As depicted in FIG. 9, the functionalization layer 902 can be disposed on or cover the insulator layer 904. The functionalization layer 902 can comprise silanes, DNA, proteins, antibodies, self-assembled mono layers (SAMs), buffered hydrogels, PVC, parylene, polyACE, or any other biochemically active materials. The functionalization layer 902 can be configured to facilitate the sensing device 800 from interacting with ions, analytes, or other molecules or byproducts in the electrolyte 204. For example, the functionalization layer 902 can be a pH-sensitive layer. In one example, the functionalization layer 902 can comprise hydroxyl groups which can interact with hydrogen ions ($H^+$) in the electrolyte 204. In another embodiment, an insulator layer 904 made of an oxide can be used as the functionalization layer 902.

An external DC bias voltage can be applied. When the light source 804 (e.g., a modulated light pointer or source) illuminates the bulk silicon, light-induced charge carriers can be separated by an internal electric field and a photocurrent can be detected by a peripheral circuit. The amplitude of the photocurrent can depend on the local surface potential.

The light source 804 can direct light 802 of specific wavelengths at the doped semiconductor layer 906. When the semiconducting material, such as silicon, in the semiconductor layer 906 absorbs light 802 matching its excitation frequency, electron-hole pairs are generated in the bulk of the semiconductor layer 906 and electrons move to the interface between the semiconductor layer 906 and the insulator layer 904 or the functionalization layer 902. As a result, a transient photocurrent can be detected by the ammeter 910. The light source 804 can modulate the wavelengths of the light 802 directed at the semiconductor layer 906 in order to induce an alternating current (AC) photocurrent.

The voltage source 908 can apply a bias voltage to the electrolyte 204 via the external reference electrode 900. This bias voltage can be applied between the semiconductor layer 906 and the reference electrode 900. The bias voltage can be set so as to repel electrons from the doped semiconductor layer 906 to form a depletion layer. The bias voltage can be set so as to repel the electrons moving to the interface between the semiconductor layer 906 and the insulator layer 904 due to the light 802 directed at the semiconductor layer 906. At a low enough bias voltage, the depletion layer is not formed. At a large enough bias voltage, the photocurrent increases until reaching a limiting value.

A bias voltage is needed to form the depletion layer. The depletion layer can, in turn, assist in the generation of a photocurrent. In the embodiment depicted in FIG. 9, the light intensity of the light source 804 is fixed so the amplitude of the photocurrent depends on the bias voltage applied. In addition, sensing the amplitude of the photocurrent depends on the local surface potential. This potential is coupled to the bias voltage applied to the sensing device 800. For example, a larger concentration of $H^+$ ions provides a larger value of this potential difference, causing the I-V curve to shift along the bias voltage axis of FIG. 10. When the bias voltage is kept constant, a change in the photocurrent can indicate a change in the pH of the electrolyte 204.

Since the bias voltage is in series with the potential at the interface between the functionalization layer 902 and the electrolyte 204, a change in the solution characteristic of the electrolyte (such as a change in analyte concentration or pH change) can change the bias voltage needed to maintain the constant photocurrent detected by the ammeter 910. For example, hydrogen ions in the solution can interact with the hydroxyl groups of the functionalization layer 902 and generate an additional potential change at the interface. This additional voltage will also cause a shift in the photocurrent, comparable to increasing or decreasing the bias voltage. In addition, hydrogen ions in the solution can also interact with the insulator layer 904 to generate a potential change at the interface and cause a shift in the photocurrent.

As shown in FIG. 8, the light source 804 can be focused so as to direct light 804 of a specific wavelength at a specific portion of the semiconductor layer 906. Moreover, a different light source or the same light source 804 can direct light 804 of a different wavelength at a different portion of the semiconductor layer 906. This allows facile multiplexing by creating a series of different sensing areas on one photocurrent sensor such that different areas of the sensor can be allocated for or dedicated to a different analyte, ion, or molecule.

Figure 10:
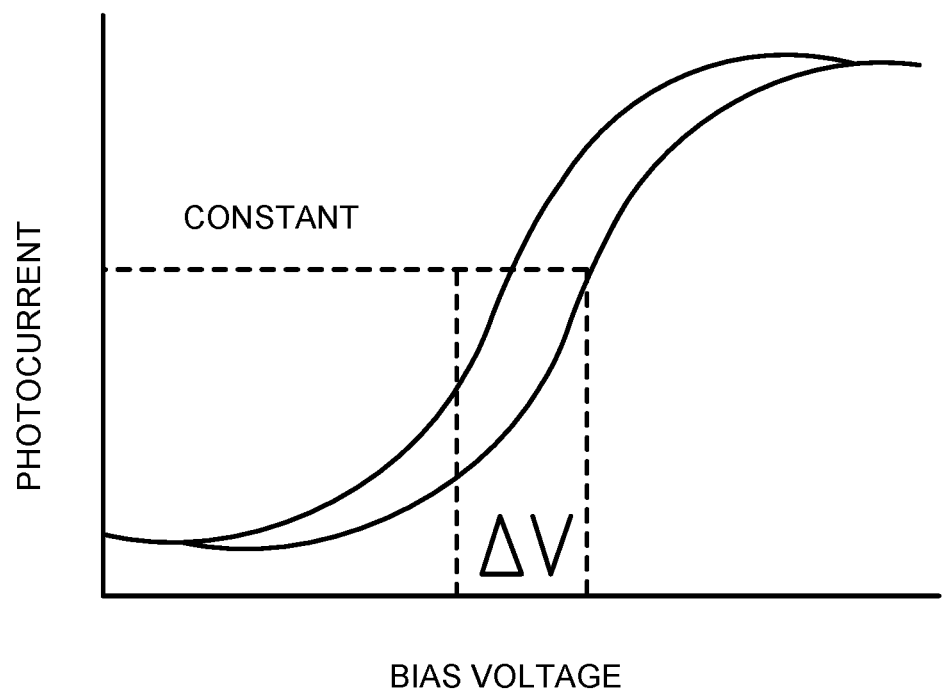
FIG. 10 illustrates an example readout from an analyzer or reader connected or communicatively coupled to the LAP sensor.

FIG. 10 illustrates one example of a photocurrent/voltage curve generated based on readings obtained from the voltage source 908 and the ammeter 910 connected to the sensing device 800. As can be seen in the photocurrent/voltage curve, a change in the solution characteristic of the electrolyte 204 over time or the difference between the solution characteristics of two different electrolytes 204 can be measured by the change in the voltage ($\Delta V$) at a constant photocurrent.

Figure 11A:
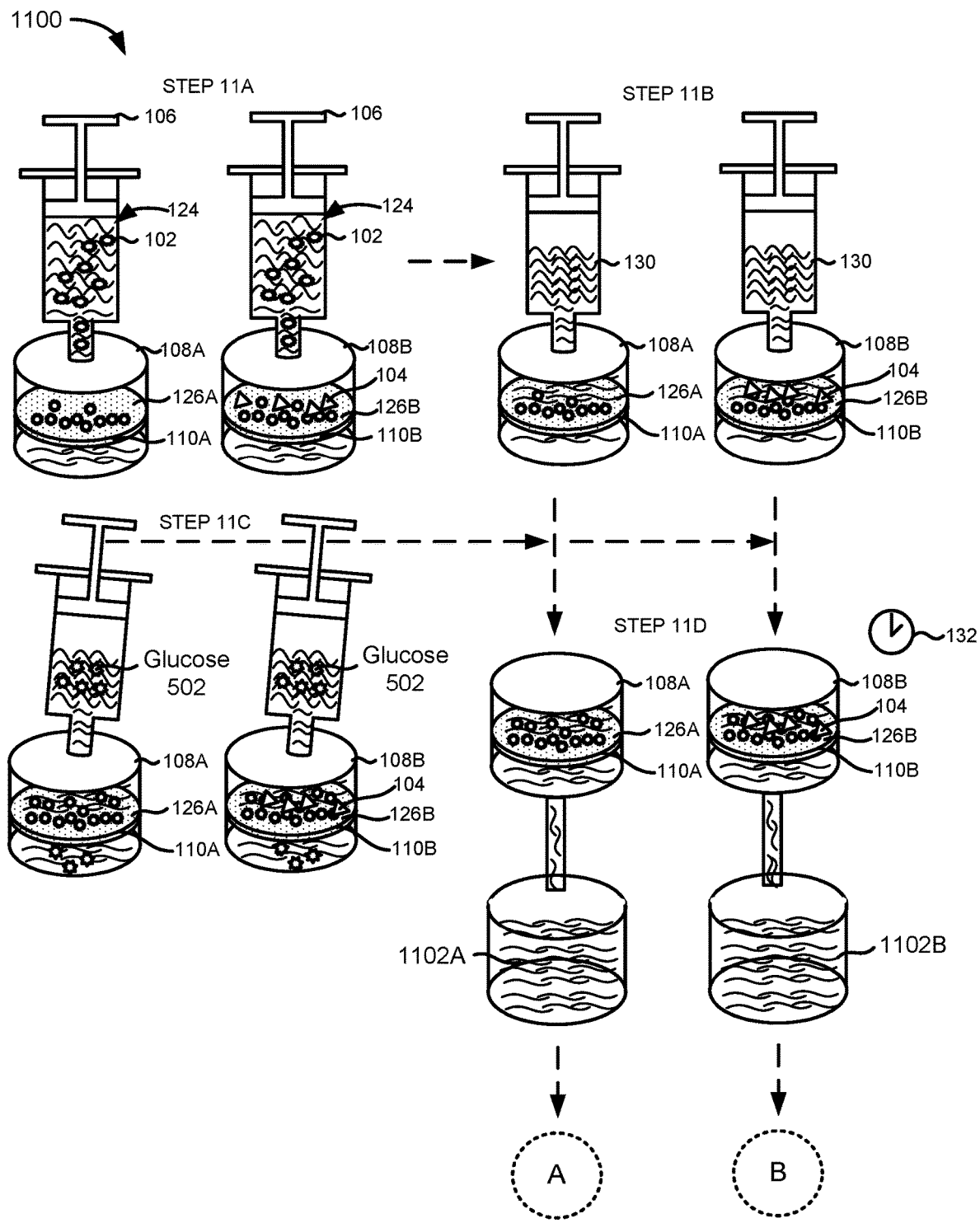
FIG. 11A illustrates one embodiment of a system for determining the susceptibility of an infectious agent to one or more anti-infectives.

FIG. 11A illustrates an embodiment of a system 1100 for assessing a susceptibility of an infectious agent 102 to an anti-infective 104. In one embodiment, the system 1100 can comprise a fluid delivery device 106, a first filter housing 108A containing a first filter 110A, a second filter housing 108B containing a second filter 110B, and a plurality of sensing devices. The sensing devices will be discussed in more detail in the sections that follow.

The system 1100 can detect or assess the level of susceptibility of the infectious agent 102 to the anti-infective 104. In some instances, the fluid sample 124 can comprise the infectious agent 102. The fluid sample 124 can include a bodily fluid such as blood, serum, plasma, urine, saliva, joint fluid, semen, wound material, spinal fluid, mucus, or a combination thereof. In other embodiments, the fluid sample 124 can also include an environmental fluid such as liquids sampled from a stream, river, lake, ocean, contamination site, quarantine zone, or emergency area. The fluid sample 124 can also be a food sample.

The infectious agent 102 can be any metabolizing single or multi-cellular organism including a bacteria or fungus. The infectious agent 102 can also be a virus or a prion. In certain embodiments, the infectious agent 102 can be a bacteria selected from the genera comprising of, but not limited to, *Acinetobacter, Aeromonas, Bacillus, Bacteroides, Citrobacter, Enterobacter, Escherichia, Klebsiella, Morganella, Pandoraea, Proteus, Providencia, Pseudomonas, Ralstonia, Raoultella, Salmonella, Serratia, Shewanella, Shigella, Stenotrophomonas, Streptomyces, Staphylococcus, Enterococcus, Clostridium* or any combination thereof. In other embodiments, the infectious agent 102 can be a fungus selected from the genera comprising of, but not limited to, *Candida, Cryptococcus*, or any combination thereof. In another embodiment, the infectious agent 102 can include amoeba. In further embodiments, the infectious agent 102 can be cancer cells and the anti-infectives 104 can be chemotherapeutics or other cancer treatments.

As illustrated in FIG. 11A, the fluid delivery device 106 can deliver or inject the fluid sample 124 into the first filter housing 108A and the second filter housing 108B in step 11A. The fluid delivery device 106 can be a pump. For example, the fluid delivery device 106 can be a hydraulic pump, a pneumatic pump, a syringe pump, or a combination thereof. In other embodiments, the fluid delivery device 106 can be an injection cartridge, a microfluidic channel, a pipette, a reaction tube, a capillary, a test tube, a combination thereof, or a portion therein.

The first filter housing 108A or the second filter housing 108B can be a container or vessel configured to secure or enclose the first filter 110A or the second filter 110B, respectively. For example, the first filter housing 108A or the second filter housing 108B can be a protective chamber. The protective chamber can be an electrically isolated environment. The protective chamber can also be a temperature controlled chamber, a light controlled chamber, or a combination thereof.

The first filter 110A can have a first filter surface 126A and the second filter 110B can have a second filter surface 126B. The first filter 110A or the second filter 110B can trap or isolate the infectious agent 102 by depositing or delivering the infectious agent 102 on to the first filter surface 126A or the second filter surface 126B, respectively. The first filter 110A or the second filter 110B can be an external surface, an internal surface extending into the filter, or a combination thereof. The first filter 110A or the second filter 110B can be made from, but is not limited to, cellulose acetate, regenerated cellulose, nylon, polystyrene, polyvinylidene fluoride (PVDF), polyethersulfone (PES), polytetrafluorethylene (PTFE), glass microfiber, or a combination thereof.

The first filter 110A or the second filter 110B can have filter pores of sequentially smaller pore size. For example, the first filter 110A or the second filter 110B can have larger filter pores at the top of the filter and progressively smaller filters pores toward the bottom of the filter. In another embodiment, the first filter 110A or the second filter 110B can have filter pores of a similar pore size throughout the entire filter. In these embodiments, the first filter surface 126A or the second filter surface 126B can be a surface of the pores. In another embodiment, the first filter 110A or the second filter 110B can be a mesh or matrix structure and the first filter surface 126A or the second filter surface 126B can be a mesh or matrix surface.

The first filter 110A or the second filter 110B can be a high-capacity filter. Although not shown in FIG. 11A, it is contemplated by this disclosure that the first filter 110A or the second filter 110B can refer to a plurality of filters in a stacked arrangement.

The first filter 110A can comprise, hold, or carry the infectious agent 102 when a fluid sample 124 comprising or carrying the infectious agent 102 is introduced to the first filter 110A. For example, the fluid sample 124 can be introduced to the first filter 110A when the fluid sample 124 is poured over or injected through the first filter 110A. The second filter 110B can also comprise, hold, or carry the infectious agent 102 when a fluid sample 124 comprising or carrying the infectious agent 102 is introduced to the second filter 110B. For example, the fluid sample 124 can be introduced to the second filter 110B when the fluid sample 124 is poured over or injected through the second filter 110B. The first filter 110A or the second filter 110B can isolate or separate the infectious agent 102 or other molecules or cells from the supernatant of the fluid sample 124.

In one embodiment, the first filter 110A or the first filter surface 126A and the second filter 110B or the second filter surface 126B can comprise the anti-infective 104. For example, the first filter 110A or the second filter 110B can comprise the anti-infective 104 when the first filter surface 126A or the second filter surface 126B is coated with the anti-infective 104 or exposed to the anti-infective 104 before introducing the fluid sample 124 to the first filter 110A or the second filter 110B. In an alternative embodiment, the anti-infective 104 can be added or introduced to the first filter 110A or the second filter 110B after exposing the first filter 110A or the second filter 110B to the fluid sample 124.

In yet another embodiment, the anti-infective 104 can be introduced through an additional solution exposed to the first filter 110A, the second filter 110B, or a combination thereof. For example, the anti-infective 104 can be introduced through a nutrient solution 130.

The anti-infective 104 can comprise a bacteriostatic anti-infective, a bactericidal anti-infective, an anti-fungal anti-infective, an antiviral anti-infective, a prion inhibitor, or a combination thereof. In another embodiment, the anti-infective 104 can be a bacterial growth inhibitor or stimulator. The bacterial growth inhibitor or stimulator can selectively inhibit or promote the growth of gram positive or gram negative bacteria. The bacterial growth inhibitor or stimulator can comprise a dye or a chemical compound. In some embodiments, the dye can include, but is not limited to, Methylene blue, Bromothymol blue, Eosin B, Safranin O, Crystal violet, or a combination thereof. The chemical compound can include, but is not limited to, sodium azide, bile acids, high sodium chloride, or a combination thereof. The anti-infective 104 can also comprise a carbon source other than glucose, such as lactose or mannose, to select for certain bacterial species. A bacterial growth inhibitor or stimulant such as urea, citrate, or certain amino acids can also be introduced to the first filter 110A, the second filter 110B, or a combination thereof.

The first filter housing 108A or the second filter housing 108B can have at least one opening which allows fluid or supernatant from the fluid sample 124 to evacuate the first filter housing 108A or the second filter housing 108B. For example, step 11A can include the additional step of discarding the fluid or supernatant from the fluid sample 124 through the opening after isolating the infectious agent 102 on the first filter surface 126A or the second filter surface 126B.

In an alternative embodiment not shown in FIG. 11A, a stimulus solution can be added to the fluid sample 124 before introducing the fluid sample 124 to the first filter 110A or the second filter 110B. The stimulus solution can be a nutrient or growth solution. The stimulus solution can have a different composition than the nutrient solution 130. The stimulus solution can be a super nutrient solution.

The fluid sample 124 can also be pre-filtered in a step before step 11A. This pre-filtering step can involve filtering the fluid sample 124 using a filter, a microfluidic filter, or a combination thereof to filter out other larger cellular components including blood cells or epithelial cells from the fluid sample 124 when the fluid sample 124 is composed of bodily fluid.

The same fluid delivery device 106 or another fluid delivery device 106 can also be used to deliver or inject nutrient solution 130 to the first filter housing 108A, the second filter housing 108B, or a combination thereof in step 11B. The fluid delivery device 106 can continuously or periodically expose the first filter surface 126A, the second filter surface 126B, or a combination thereof to the nutrient solution 130.

After exposing the first filter 110A or the second filter 110B to the nutrient solution 130, another fluid delivery device 106 or the same fluid delivery device 106 can be used to deliver or inject a known concentration of glucose 502 to the first filter housing 108A or the first filter 110A, the second filter housing 108B or the second filter 110B, or a combination thereof in an optional step 11C.

The first filter 110A, the second filter 110B, or a combination thereof can be heated to a temperature of between 30° C. and 40° C. and allowed to incubate for an incubation period 132 in step 11D. In one embodiment, the first filter 110A or the second filter 110B can be incubated while in the first filter housing 108A or the second filter housing 108B, respectively. In another embodiment, the first filter 110A or the second filter 110B can be removed from the first filter housing 108A or the second filter housing 108B, respectively, prior to incubation. In some embodiments, the first filter 110A, the second filter 110B, or a combination thereof can be incubated with the nutrient solution 130 and the known concentration of glucose 502. In other embodiments, the first filter 110A, the second filter 110B, or a combination thereof can be incubated with the nutrient solution 130.

In some embodiments, the incubation period 132 can range from 15 minutes to over one hour. In other embodiments, the incubation period 132 can be less than 15 minutes. When glucose 502 is added to the system 1100, the incubation period 132 can range from one hour to five hours. In other embodiments involving exogenous glucose 502, the incubation period 132 can exceed five hours. The incubation period 132 can be adjusted based on the type of infectious agent 102, such as the type of bacteria, fungus, virus, or prion suspected in the fluid sample 124.

The incubation period 132 can also be adjusted based on the suspected amount of the infectious agent 102 present in the fluid sample 124, the amount or volume of the fluid sample 124, the amount of glucose 502 added, or a combination thereof. For example, the incubation period 132 can be increased when the amount of the infectious agent 102 is below a threshold amount. The first filter 110A or the second filter 110B can be allowed to incubate with the nutrient solution 130 in order to promote the proliferation of the infectious agent 102 on the first filter surface 126A or the second filter surface 126B.

One advantage of incubating the first filter 110A and the second filter 110B is to increase the sensitivity of the system 1100 to small amounts of the infectious agent 102. For example, incubating the first filter 110A and the second filter 110B can allow the system 1100 to reduce its level of detection.

After incubating the first filter 110A or the second filter 110B, the effluent or outflow of the nutrient solution 130 and/or the solution of glucose 502 exposed to the first filter 110A or the second filter 110B can be sampled. The effluent or outflow of the nutrient solution 130 and/or the solution of glucose 502 exposed to the first filter 110A can be referred to as the first sample effluent 1102A. The effluent or outflow of the nutrient solution 130 and/or the solution of glucose 502 exposed to the second filter 110B can be referred to as the second sample effluent 1102B. The first sample effluent 1102A can be the sample effluent 134A depicted in FIGS. 1 and 8 when glucose 502 is not added to the system 1100 or the sample effluent 504 depicted in FIG. 5 when glucose 502 is added to the system 110. The second sample effluent 1102B can be the sample effluent 134 depicted in FIGS. 1 and 8 when glucose 502 is not added to the system 1100 or the sample effluent 504 depicted in FIG. 5 when glucose 502 is added to the system 110.

The steps depicted in FIG. 11A do not require the particular order shown to achieve the desired result and certain steps or processes may occur in parallel.

Figure 11B:
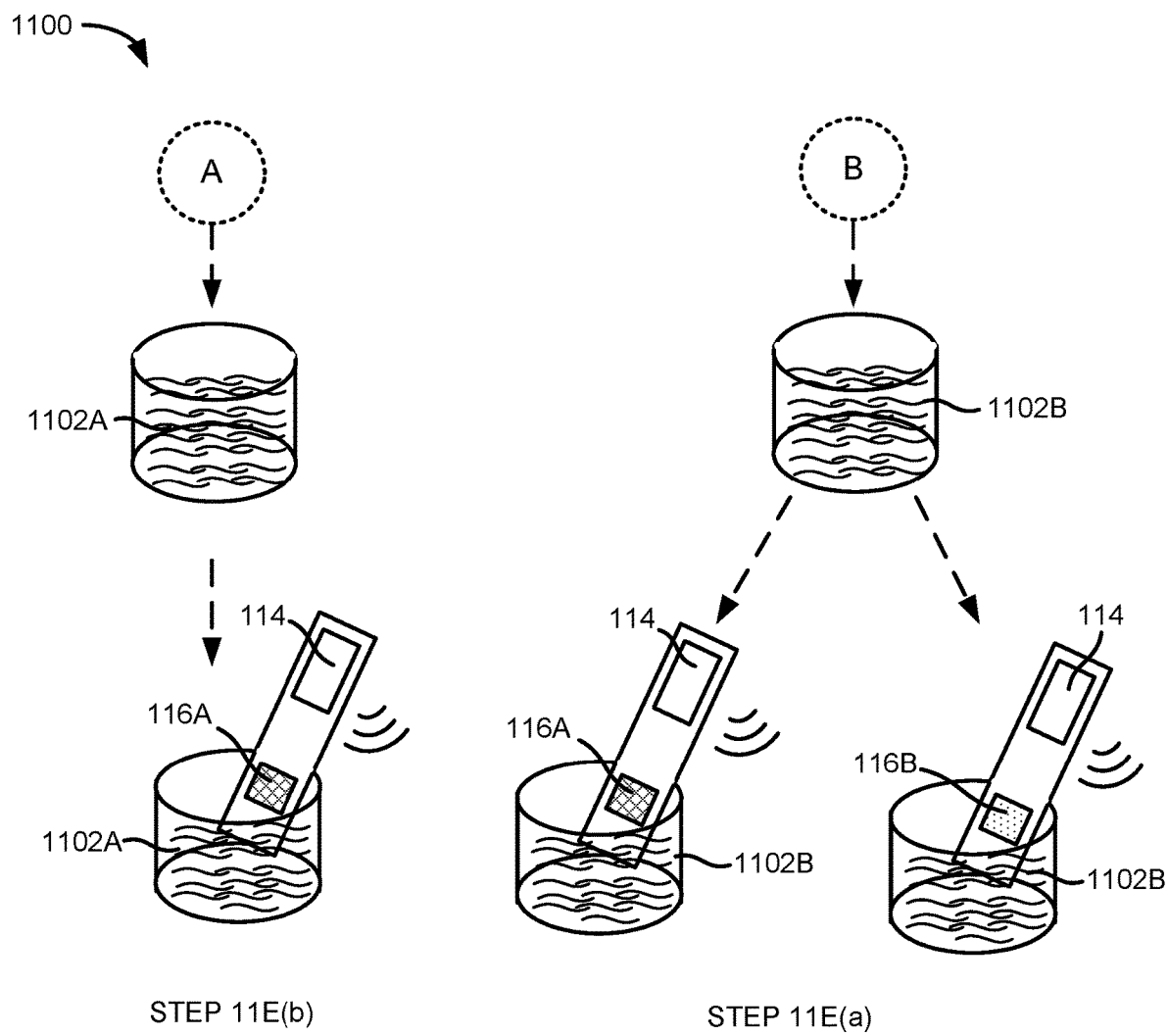
FIG. 11B illustrates a variation of the system from FIG. 11A using electrochemical cells.
Figure 11B:

FIG. 11B illustrates a variation of the system 1100 of FIG. 11A using electrochemical sensors. As depicted in FIG. 11B, the system 1100 of FIG. 11A can further comprise a first sensing device 116A, a second sensing device 116B, or a combination thereof. Any of the first sensing device 116A or the second sensing device 116B can be the sensing device 116 of FIG. 1, 2A, 2B, 3A, or 3B. For example, any of the first sensing device 116A or the second sensing device 116B can be the electrochemical cell shown in FIG. 2A, 2B, 3A, or 3B.

The first sample effluent 1102A can be analyzed by the first sensing device 116A and the second sample effluent 1102B can be analyzed by the second sensing device 116B in step 11E(a). As depicted in FIG. 11B, in one embodiment, the first sample effluent 1102A can be analyzed by inserting a portion of the first sensing device 116A directly into the first sample effluent 1102A and the second sample effluent 1102B can be analyzed by inserting a portion of the second sensing device 116B directly into the second sample effluent 1102B. In an alternative embodiment not shown in FIG. 11B but contemplated by the disclosure, the first sample effluent 1102A can be analyzed by applying or introducing an aliquot of the first sample effluent 1102A to the first sensing device 116A and the second sample effluent 1102B can be analyzed by applying or introducing an aliquot of the second sample effluent 1102B to the second sensing device 116B.

In another embodiment shown in FIG. 11B, the same first sensing device 116A can be used to analyze the first sample effluent 1102A and the second sample effluent 1102B in step 11E(b). In this embodiment, the first sensing device 116A can be cleaned or recalibrated after each analysis or use.

The first sample effluent 1102A and the second sample effluent 1102B can each comprise a solution characteristic. The solution characteristic can refer to one or more attributes of the solution making up the first sample effluent 1102A, the second sample effluent 1102B, or a combination thereof. For example, the solution characteristic can include a concentration of a solute, analyte, or molecule, an absolute number or molecular count of solutes, analytes, or molecules in solution, a solution temperature, or a combination thereof. For example, the solution characteristic can refer to the amount or concentration of ions, organic molecules such as amino acids, vitamins or glucose, minerals, or other inorganic compounds in the first sample effluent 1102A, the second sample effluent 1102B, or a combination thereof.

The solution characteristic can vary as a result of ions, molecules, minerals, or nutrients produced by, consumed by, or otherwise attributed to the infectious agent 102 on the first filter surface 126A, the second filter surface 126B, or a combination thereof. In one embodiment, the first sample effluent 1102A, the second sample effluent 1102B, or a combination thereof can comprise hydrogen ions ($H^+$) as a byproduct of bacterial cell metabolism or growth. In this embodiment, the concentration or amount of hydrogen ions (($H^+$) can change over time in one sample effluent (e.g., in the first sample effluent 1102A) or differ between the first sample effluent 1102A and the second sample effluent 1102B based on the presence, proliferation, or activity of the infectious agent 102 exposed to the first sample effluent 1102A, the second sample effluent 1102B, or a combination thereof.

In other embodiments, the first sample effluent 1102A, the second sample effluent 1102B, or a combination thereof can comprise differing or changing concentrations or amounts of adenosine triphosphate (ATP), carbon dioxide ($CO_2$), lactic acid, carbonic acid, nitrates ($NO_3^-$), or a combination thereof attributed to the infectious agent 102.

A change in the solution characteristic can cause a change in the electrical characteristic of the first sensing device 116A, the second sensing device 116B, or a combination thereof. A parameter analyzer 114 can monitor the electrical characteristic of the first sensing device 116A, the second sensing device 116B, or a combination thereof.

As depicted in FIG. 11B, the parameter analyzer 114 can be integrated into one device with the first sensing device 116A, the second sensing device 116B, or a combination thereof. For example, the parameter analyzer 114 can be fabricated on the same substrate as the first sensing device 116A, the second sensing device 116B, or a combination thereof. In other embodiments not shown in FIG. 11B, the parameter analyzer 114 can be a standalone unit or device coupled to the first sensing device 116A, the second sensing device 116B, or a combination thereof.

The parameter analyzer 114 can monitor a first electrical characteristic of the first sensing device 116A exposed to the first sample effluent 1102A. Another parameter analyzer 114 or the same parameter analyzer 114 can monitor a second electrical characteristic of the second sensing device 116B exposed to the second sample effluent 1102B.

The electrical characteristic, including the first electrical characteristic and the second electrical characteristic, can include, but is not limited to, a voltage, a current, an impedance, a resistance, a capacitance, a resonant frequency, a noise level, a level of induction, or a combination thereof measured at or near the first sensing device 116A, the second sensing device 116B, or a combination thereof. The change in the electrical characteristic can include, but is not limited to, a voltage change, an impedance change, a current change, a capacitance change, a resistance change, a change in resonant frequency, a noise level change, an induction change, or a combination thereof measured at or near the first sensing device 116A, the second sensing device 116B, or a combination thereof.

In one embodiment, the parameter analyzer 114 can be a voltage meter. In other embodiments, the parameter analyzer 114 can be, but is not limited to, a multimeter, an ammeter, a capacitance analyzer, or a combination thereof.

For example, monitoring the first electrical characteristic can involve determining a first voltage change at a first functionalization layer (such as the functionalization layer 208 in FIG. 2A, 2B, 3A, or 3B) of the first sensing device 116A exposed to the first sample effluent 1102A. The first voltage change can be with respect to a voltage at a first reference electrode (such as either the external reference electrode 202 of FIGS. 2A and 3A or the on-chip reference electrode of FIGS. 2B and 3B) of the first sensing device 116A exposed to the first sample effluent 1102A. In these example embodiments, the first functionalization layer can cover the working electrode depicted in FIG. 2A or 3A or cover the working electrode 214 of the first sensing device 116A.

Also, for example, monitoring the second electrical characteristic can involve determining a second voltage change at a second functionalization layer (such as the functionalization layer 208 in FIG. 2A, 2B, 3A, or 3B) of the second sensing device 116B exposed to the second sample effluent 1102B. The second voltage change can be with respect to a voltage at a second reference electrode (such as either the external reference electrode 202 of FIGS. 2A and 3A or the on-chip reference electrode of FIGS. 2B and 3B) of the second sensing device 116B exposed to the second sample effluent 1102B. In these example embodiments, the second functionalization layer can cover the working electrode of the second sensing device 116B.

When only one sensing device (such as the first sensing device 116A) is used to sample the sample effluents, the parameter analyzer 114 can monitor the electrical characteristic of the first sensing device 116A exposed to the first sample effluent 1102A and the electrical characteristic of the same first sensing device 116A exposed to the second sample effluent 1102B. In this embodiment, the electrical characteristic of the first sensing device 116A while sampling the first sample effluent 1102A can be referred to as the first electrical characteristic and the electrical characteristic of the first sensing device 116A while sampling the second sample effluent 1102B can be referred to as the second electrical characteristic.

The parameter analyzer 114 can compare the first electrical characteristic, including a change in the first electrical characteristic, with the second electrical characteristic, including a change in the second electrical characteristic, to assess the susceptibility of the infectious agent 102 to the anti-infective 104. In some embodiments, the first electrical characteristic can differ from the second electrical characteristic when the solution characteristic of the first sample effluent 1102A differs from the solution characteristic of the second sample effluent 1102B as a result of differences in the concentration or amount of ions, analytes, molecules, minerals, or other solutes present in the sample effluents.

For example, the first electrical characteristic and the second electrical characteristic can differ when the solution characteristic of the first sample effluent 1102A and the solution characteristic of the second sample effluent differ in their pH. In other embodiments, the first electrical characteristic can differ from the second electrical characteristic when the solution characteristic of the first sample effluent 1102A differs from the solution characteristic of the second sample effluent 1102B as a result of differences in the temperature of the solution.

In one embodiment, the parameter analyzer 114 can assess the susceptibility of the infectious agent 102 to the anti-infective 104 as a binary assessment or a tiered assessment. In another embodiment, a reader or computing device connected or communicatively coupled to the parameter analyzer 114 can assess the susceptibility of the infectious agent 102 to the anti-infective 104 as a binary assessment or a tiered assessment.

The parameter analyzer 114 or the reader communicatively coupled to the parameter analyzer 114 can assess the susceptibility of the infectious agent 102 as either resistant or non-resistant to the anti-infective 104. In this embodiment, the second filter 110B or the second filter surface 126B can comprise a set amount of the anti-infective 104. The parameter analyzer 114 or a reader communicatively coupled to the parameter analyzer 114 can then assess the susceptibility of the infectious agent 102 as either resistant or non-resistant based on any detected differences in the first electrical characteristic and the second electrical characteristic or any detected differences in the change in the first electrical characteristic and the change in the second electrical characteristic.

The parameter analyzer 114 or the reader communicatively coupled to the parameter analyzer 114 can assess the susceptibility of the infectious agent 102 as not resistant to the anti-infective 104 when the parameter analyzer 114 or the reader fails to detect a difference or a statistically significant difference between the first electrical characteristic and the second electrical characteristic or a statistically significant difference between the change in the first electrical characteristic and the change in the second electrical characteristic. More specifically, a statistically significant difference in the electrical characteristic can be a difference exceeding a threshold value.

In other embodiments, the parameter analyzer 114 or the reader communicatively coupled to the parameter analyzer 114 can assess the level of susceptibility of the infectious agent 102 on a tiered scale. For example, the parameter analyzer 114 or the reader communicatively coupled to the parameter analyzer 114 can assess the susceptibility of the infectious agent 102 as being resistant, mildly susceptible, or susceptible to the anti-infective 104. In these embodiments, additional filter surfaces, including a third filter surface, can be used which comprise anti-infectives 104 of different concentrations. While three categories of susceptibility are discussed, it should be understood by one of ordinary skill in the art that four or greater categories of susceptibility or four or more filters can be used to assess the level of susceptibility of the infectious agent 102 to differing concentrations of the anti-infective 104.

The parameter analyzer 114 can also have or be connected to a display 113 or display component configured to provide a result of the detection or a read-out of the electrical characteristic of the first sensing device 116A, the second sensing device 116B, or a combination thereof. In some embodiments, the parameter analyzer 114 can be a mobile device, a handheld device, a tablet device, or a computing device such as a laptop or desktop computer and the display 113 can be a mobile device display, a handheld device display, a tablet display, or a laptop or desktop monitor.

In one embodiment, the parameter analyzer 114 can display a result indicating the level of susceptibility of the infectious agent 102 in the fluid sample 124 via the display 113. In another embodiment, the parameter analyzer 114 can wirelessly communicate a result indicating the presence of an infectious agent 102 in the fluid sample 124 to a computing device having the display 113.

Figure 11C:
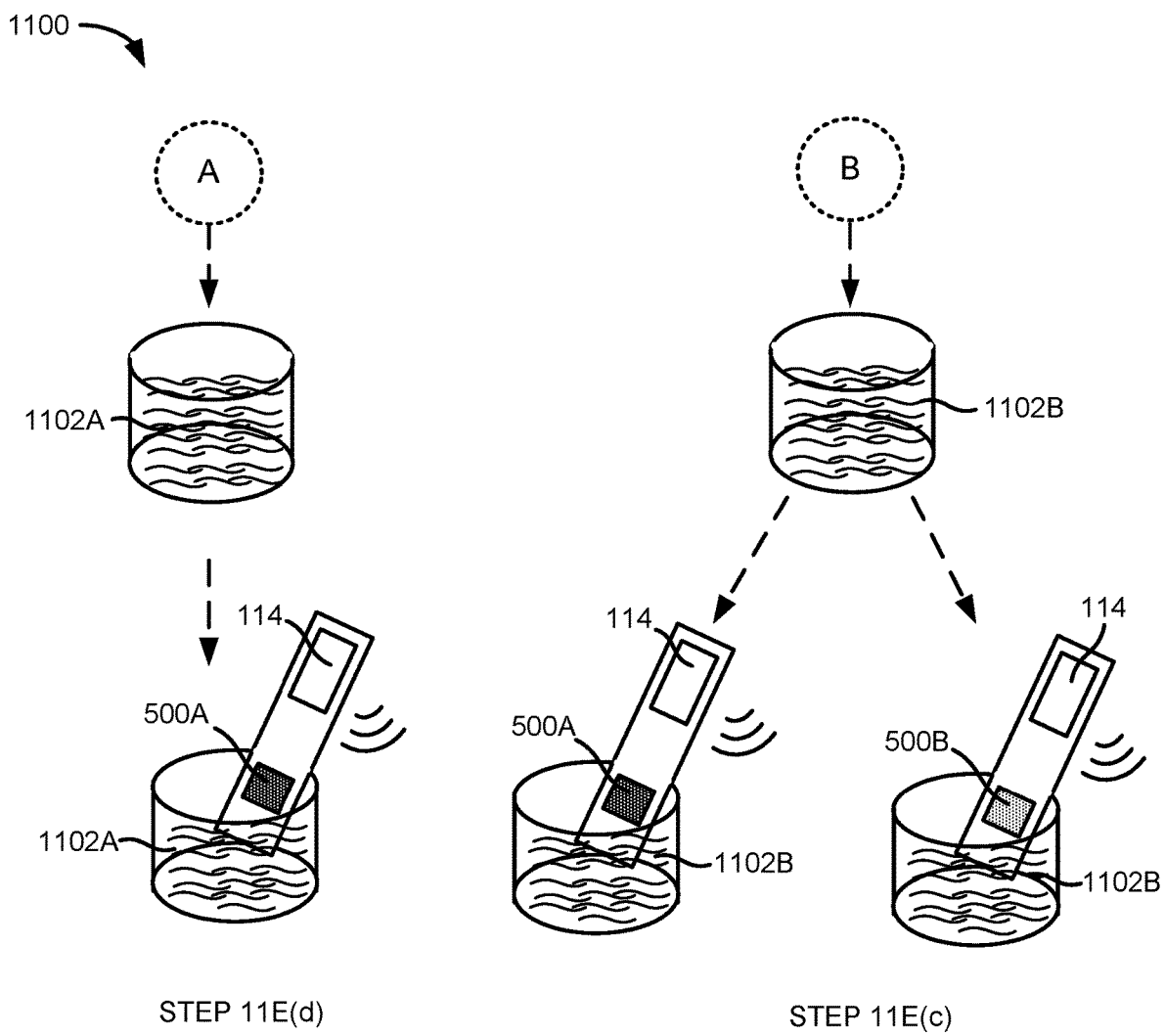
FIG. 11C illustrates another variation of the system from FIG. 11A using glucose sensors.
Figure 11C:

FIG. 11C illustrates a variation of the system of FIG. 11A using glucose sensors. As depicted in FIG. 11C, the system 1100 of FIG. 11A can further comprise a first sensing device 500A, a second sensing device 500B, or a combination thereof. Any of the first sensing device 500A or the second sensing device 500B can be the sensing device 500 of FIG. 5. For example, any of the first sensing device 500A or the second sensing device 500B can be the glucose sensor shown in FIG. 5.

The first sample effluent 1102A can be analyzed by the first sensing device 500A and the second sample effluent 1102B can be analyzed by the second sensing device 500B in step 11E(c). As depicted in FIG. 11C, in one embodiment, the first sample effluent 1102A can be analyzed by inserting a portion of the first sensing device 500A directly into the first sample effluent 1102A and the second sample effluent 1102B can be analyzed by inserting a portion of the second sensing device 500B directly into the second sample effluent 1102B. In an alternative embodiment not shown in FIG. 11C but contemplated by the disclosure, the first sample effluent 1102A can be analyzed by applying or introducing an aliquot of the first sample effluent 1102A to the first sensing device 500A and the second sample effluent 1102B can be analyzed by applying or introducing an aliquot of the second sample effluent 1102B to the second sensing device 500B.

In another embodiment shown in FIG. 11C, the same first sensing device 500A can be used to analyze the first sample effluent 1102A and the second sample effluent 1102B in step 11E(d). In this embodiment, the first sensing device 500A can be cleaned or recalibrated after each analysis or use.

The first sample effluent 1102A and the second sample effluent 1102B can each comprise a solution characteristic. The solution characteristic can refer to one or more attributes of the solution making up the first sample effluent 1102A, the second sample effluent 1102B, or a combination thereof. For example, the solution characteristic can include a concentration of a solute, analyte, or molecule, an absolute number or molecular count of solutes, analytes, or molecules in solution, a solution temperature, or a combination thereof. For example, the solution characteristic can refer to the amount or concentration of ions, organic molecules such as amino acids, vitamins or glucose, minerals, or other inorganic compounds in the first sample effluent 1102A, the second sample effluent 1102B, or a combination thereof.

The solution characteristic can vary as a result of nutrients consumed by the infectious agent 102 on the first filter surface 126A, the second filter surface 126B, or a combination thereof. For example, as depicted in step 11C, a known concentration of glucose 502 can be added to the first filter housing 108A, the first filter 110A, the second filter housing 108B, the second filter 110B, or a combination thereof.

After the incubation period 132, the concentration of glucose 502 in the first sample effluent 1102A can differ from the concentration of glucose 502 in the second sample effluent 1102B based on the presence, proliferation, or activity of the infectious agent 102 on the first filter surface 126A, the second filter surface 126B, or a combination thereof.

A change in the glucose concentration can cause a change in the electrical characteristic of the first sensing device 500A, the second sensing device 500B, or a combination thereof. A parameter analyzer 114 can monitor the electrical characteristic of the first sensing device 500A, the second sensing device 500B, or a combination thereof.

As depicted in FIG. 11C, the parameter analyzer 114 can be integrated into one device with the first sensing device 500A, the second sensing device 500B, or a combination thereof. For example, the parameter analyzer 114 can be fabricated on the same substrate as the first sensing device 500A, the second sensing device 500B, or a combination thereof. In other embodiments not shown in FIG. 11C, the parameter analyzer 114 can be a standalone unit or device coupled to the first sensing device 500A, the second sensing device 500B, or a combination thereof.

The parameter analyzer 114 can monitor a first electrical characteristic of the first sensing device 500A exposed to the first sample effluent 1102A. Another parameter analyzer 114 or the same parameter analyzer 114 can monitor a second electrical characteristic of the second sensing device 500B exposed to the second sample effluent 1102B.

The electrical characteristic, including the first electrical characteristic and the second electrical characteristic, can include, but is not limited to, a voltage, a current, an impedance, a resistance, a capacitance, a resonant frequency, a noise level, a level of induction, or a combination thereof measured at or near the first sensing device 500A, the second sensing device 500B, or a combination thereof. The change in the electrical characteristic can include, but is not limited to, a voltage change, an impedance change, a current change, a capacitance change, a resistance change, a change in resonant frequency, a noise level change, an induction change, or a combination thereof measured at or near the first sensing device 500A, the second sensing device 500B, or a combination thereof.

In one embodiment, the parameter analyzer 114 can include a voltage meter and an ammeter. In other embodiments, the parameter analyzer 114 can be, but is not limited to, a multimeter, a singular voltage meter, a singular ammeter, a capacitance analyzer, or a combination thereof.

When only one sensing device (such as the first sensing device 500A) is used to sample the sample effluents, the parameter analyzer 114 can monitor the electrical characteristic of the first sensing device 500A exposed to the first sample effluent 1102A and the electrical characteristic of the same first sensing device 500A exposed to the second sample effluent 1102B. In this embodiment, the electrical characteristic of the first sensing device 500A while sampling the first sample effluent 1102A can be referred to as the first electrical characteristic and the electrical characteristic of the first sensing device 500A while sampling the second sample effluent 1102B can be referred to as the second electrical characteristic.

The parameter analyzer 114 can compare the first electrical characteristic, including a change in the first electrical characteristic, with the second electrical characteristic, including a change in the second electrical characteristic, to assess the susceptibility of the infectious agent 102 to the anti-infective 104. In some embodiments, the first electrical characteristic can differ from the second electrical characteristic when the solution characteristic of the first sample effluent 1102A differs from the solution characteristic of the second sample effluent 1102B as a result of differences in the concentration or amount of a nutrient added to the system 1100. For example, the first electrical characteristic and the second electrical characteristic can differ when the glucose concentration of the first sample effluent 1102A and the glucose concentration of the second sample effluent differ.

In one embodiment, the parameter analyzer 114 can assess the susceptibility of the infectious agent 102 to the anti-infective 104 as a binary assessment or a tiered assessment. In another embodiment, a reader or computing device connected or communicatively coupled to the parameter analyzer 114 can assess the susceptibility of the infectious agent 102 to the anti-infective 104 as a binary assessment or a tiered assessment.

The parameter analyzer 114 or the reader communicatively coupled to the parameter analyzer 114 can assess the susceptibility of the infectious agent 102 as either resistant or non-resistant to the anti-infective 104. In this embodiment, the second filter 110B or the second filter surface 126B can comprise a set amount of the anti-infective 104. The parameter analyzer 114 or a reader communicatively coupled to the parameter analyzer 114 can then assess the susceptibility of the infectious agent 102 as either resistant or non-resistant based on any detected differences in the first electrical characteristic and the second electrical characteristic or any detected differences in the change in the first electrical characteristic and the change in the second electrical characteristic.

The parameter analyzer 114 or the reader communicatively coupled to the parameter analyzer 114 can assess the susceptibility of the infectious agent 102 as not resistant to the anti-infective 104 when the parameter analyzer 114 or the reader fails to detect a difference or a statistically significant difference between the first electrical characteristic and the second electrical characteristic or a statistically significant difference between the change in the first electrical characteristic and the change in the second electrical characteristic. More specifically, a statistically significant difference in the electrical characteristic can be a difference exceeding a threshold value.

In other embodiments, the parameter analyzer 114 or the reader communicatively coupled to the parameter analyzer 114 can assess the level of susceptibility of the infectious agent 102 on a tiered scale. For example, the parameter analyzer 114 or the reader communicatively coupled to the parameter analyzer 114 can assess the susceptibility of the infectious agent 102 as being resistant, mildly susceptible, or susceptible to the anti-infective 104. In these embodiments, additional filter surfaces, including a third filter surface, can be used which comprise anti-infectives 104 of different concentrations. While three categories of susceptibility are discussed, it should be understood by one of ordinary skill in the art that four or greater categories of susceptibility or four or more filters can be used to assess the level of susceptibility of the infectious agent 102 to differing concentrations of the anti-infective 104.

The parameter analyzer 114 can also have or be connected to a display 113 or display component configured to provide a result of the detection or a read-out of the electrical characteristic of the first sensing device 500A, the second sensing device 500B, or a combination thereof. In some embodiments, the parameter analyzer 114 can be a mobile device, a handheld device, a tablet device, or a computing device such as a laptop or desktop computer and the display 113 can be a mobile device display, a handheld device display, a tablet display, or a laptop or desktop monitor.

In one embodiment, the parameter analyzer 114 can display a result indicating the level of susceptibility of the infectious agent 102 in the fluid sample 124 via the display 113. In another embodiment, the parameter analyzer 114 can wirelessly communicate a result indicating the presence of an infectious agent 102 in the fluid sample 124 to a computing device having the display 113.

Figure 11D:
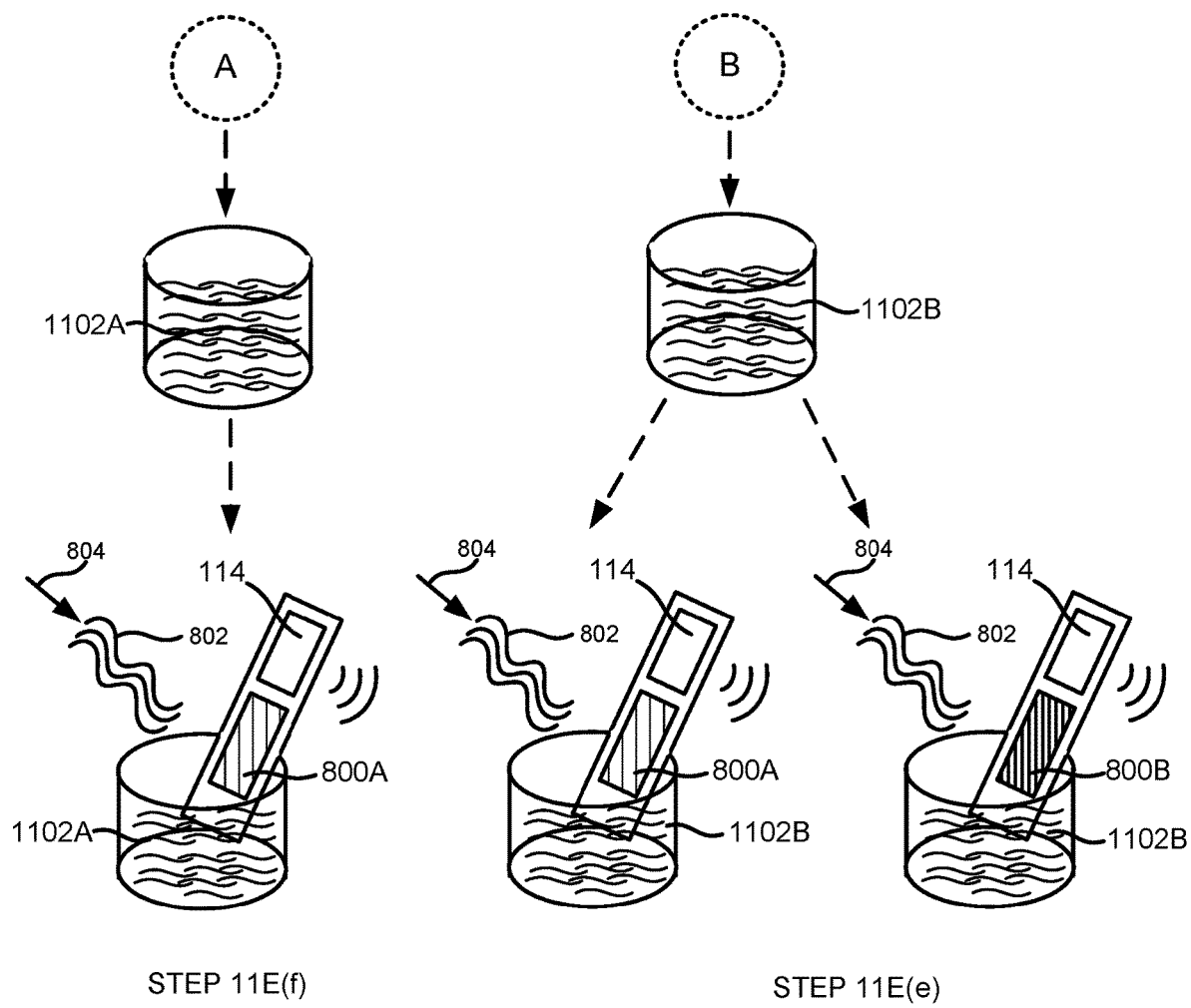
FIG. 11D illustrates another variation of the system from FIG. 11A using LAP sensors.
Figure 11D:
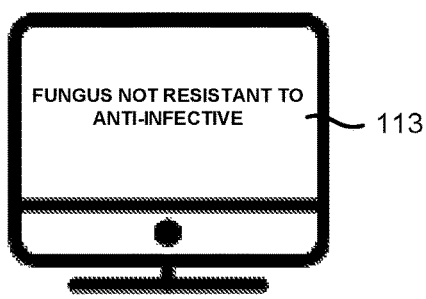

FIG. 11D illustrates a variation of the system of FIG. 11A using light-addressable potentiometric (LAP) sensors. As depicted in FIG. 11D, the system 1100 of FIG. 11A can further comprise a first sensing device 800A, a second sensing device 800B, or a combination thereof. Any of the first sensing device 800A or the second sensing device 800B can be the sensing device 800 of FIG. 8. For example, any of the first sensing device 800A or the second sensing device 800B can be the photocurrent or LAP sensor shown in FIG. 8.

The first sample effluent 1102A can be analyzed by the first sensing device 800A and the second sample effluent 1102B can be analyzed by the second sensing device 800B in step 11E(e). As depicted in FIG. 11D, in one embodiment, the first sample effluent 1102A can be analyzed by inserting a portion of the first sensing device 800A directly into the first sample effluent 1102A and the second sample effluent 1102B can be analyzed by inserting a portion of the second sensing device 800B directly into the second sample effluent 1102B. In an alternative embodiment not shown in FIG. 11C but contemplated by the disclosure, the first sample effluent 1102A can be analyzed by applying or introducing an aliquot of the first sample effluent 1102A to the first sensing device 800A and the second sample effluent 1102B can be analyzed by applying or introducing an aliquot of the second sample effluent 1102B to the second sensing device 800B.

In another embodiment shown in FIG. 11D, the same first sensing device 800A can be used to analyze the first sample effluent 1102A and the second sample effluent 1102B in step 11E(f). In this embodiment, the first sensing device 800A can be cleaned or recalibrated after each analysis or use.

The first sample effluent 1102A and the second sample effluent 1102B can each comprise a solution characteristic. The solution characteristic can refer to one or more attributes of the solution making up the first sample effluent 1102A, the second sample effluent 1102B, or a combination thereof. For example, the solution characteristic can include a concentration of a solute, analyte, or molecule, an absolute number or molecular count of solutes, analytes, or molecules in solution, a solution temperature, or a combination thereof. For example, the solution characteristic can refer to the amount or concentration of ions, organic molecules such as amino acids, vitamins or glucose, minerals, or other inorganic compounds in the first sample effluent 1102A, the second sample effluent 1102B, or a combination thereof.

The solution characteristic can vary as a result of ions, molecules, minerals, or nutrients produced by, consumed by, or otherwise attributed to the infectious agent 102 on the first filter surface 126A, the second filter surface 126B, or a combination thereof. In one embodiment, the first sample effluent 1102A, the second sample effluent 1102B, or a combination thereof can comprise hydrogen ions (H$^+$) as a byproduct of bacterial cell metabolism or growth. In this embodiment, the concentration or amount of hydrogen ions ((H$^+$) can change over time in one sample effluent (e.g., in the first sample effluent 1102A) or differ between the first sample effluent 1102A and the second sample effluent 1102B based on the presence, proliferation, or activity of the infectious agent 102 exposed to the first sample effluent 1102A, the second sample effluent 1102B, or a combination thereof.

In other embodiments, the first sample effluent 1102A, the second sample effluent 1102B, or a combination thereof can comprise differing or changing concentrations or amounts of adenosine triphosphate (ATP), carbon dioxide ($CO_2$), lactic acid, carbonic acid, nitrates ($NO_3^-$), or a combination thereof attributed to the infectious agent 102.

A change in the solution characteristic can cause a change in the electrical characteristic of the first sensing device 800A, the second sensing device 800B, or a combination thereof. A parameter analyzer 114 can monitor the electrical characteristic of the first sensing device 800A, the second sensing device 800B, or a combination thereof. In one embodiment, the parameter analyzer 114 can include voltage source 908 and the ammeter 910 of FIG. 9. In other embodiments, the parameter analyzer 114 can include a voltmeter, a multimeter, a capacitance analyzer, or a combination thereof.

As depicted in FIG. 11D, the parameter analyzer 114 can be integrated into one device with the first sensing device 800A, the second sensing device 800B, or a combination thereof. For example, the parameter analyzer 114 can be fabricated on the same substrate as the first sensing device 800A, the second sensing device 800B, or a combination thereof. In other embodiments not shown in FIG. 11D, the parameter analyzer 114 can be a standalone unit or device coupled to the first sensing device 800A, the second sensing device 800B, or a combination thereof.

The parameter analyzer 114 can monitor a first electrical characteristic of the first sensing device 800A exposed to the first sample effluent 1102A. Another parameter analyzer 114 or the same parameter analyzer 114 can monitor a second electrical characteristic of the second sensing device 800B exposed to the second sample effluent 1102B.

The electrical characteristic, including the first electrical characteristic and the second electrical characteristic, can include, but is not limited to, a voltage, a current, an impedance, a resistance, a capacitance, a resonant frequency, a noise level, a level of induction, or a combination thereof measured at or near the first sensing device 800A, the second sensing device 800B, or a combination thereof. The change in the electrical characteristic can include, but is not limited to, a voltage change, an impedance change, a current change, a capacitance change, a resistance change, a change in resonant frequency, a noise level change, an induction change, or a combination thereof measured at or near the first sensing device 800A, the second sensing device 800B, or a combination thereof.

As depicted in FIG. 11D, a light source 804 can direct light 802 of specific wavelengths at the doped semiconductor layer 906 (see FIG. 9) of the first sensing device 800A, the second sensing device 800B, or a combination thereof. When the semiconducting material, such as silicon, in the semiconductor layer 906 absorbs light 802 matching its excitation frequency, electron-hole pairs are generated in the bulk of the semiconductor layer 906 and electrons move to the interface between the semiconductor layer 906 and the insulator layer 904. As a result, a transient photocurrent can be detected by the parameter analyzer 114. The light source 804 can modulate the wavelengths of the light 802 directed at the semiconductor layer 906 in order to induce an alternating current (AC) photocurrent.

The parameter analyzer 114 can also apply a bias voltage to the first sample effluent 1102A, the second sample effluent 1102B, or a combination thereof via an external reference electrode (such as the external reference electrode 900 of FIG. 9). The bias voltage can be set so as to repel electrons from the doped semiconductor layer of the first sensing device 800A, the second sensing device 800B, or a combination thereof to form a depletion layer. The bias voltage can be set so as to repel the electrons moving to the interface between the semiconductor layer and the insulator layer due to the light 802 directed at the semiconductor layer. At a low enough bias voltage, the depletion layer is not formed. At a large enough bias voltage, the photocurrent increases until reaching a limiting value.

A change in the solution characteristic of the first sample effluent 1102A, the second sample effluent 1102B, or a combination thereof (such as a change in analyte concentration or pH change) can change the bias voltage needed to maintain the constant photocurrent detected by the parameter analyzer 114.

When only one sensing device (such as the first sensing device 800A) is used to sample the sample effluents, the parameter analyzer 114 can monitor the electrical characteristic of the first sensing device 800A exposed to the first sample effluent 1102A and the electrical characteristic of the same first sensing device 800A exposed to the second sample effluent 1102B. In this embodiment, the electrical characteristic of the first sensing device 800A while sampling the first sample effluent 1102A can be referred to as the first electrical characteristic and the electrical characteristic of the first sensing device 800A while sampling the second sample effluent 1102B can be referred to as the second electrical characteristic.

The parameter analyzer 114 can compare the first electrical characteristic (such as the bias voltage applied to the first sensing device 800A), including a change in the first electrical characteristic (such as a change in the bias voltage needed to maintain a constant photocurrent at the first sensing device 800A), with the second electrical characteristic (such as the bias voltage applied to the second sensing device 800B), including a change in the second electrical characteristic (such as a change in the bias voltage needed to maintain a constant photocurrent at the second sensing device 800B), to assess the susceptibility of the infectious agent 102 to the anti-infective 104. In some embodiments, the first electrical characteristic can differ from the second electrical characteristic when the solution characteristic of the first sample effluent 1102A differs from the solution characteristic of the second sample effluent 1102B as a result of differences in the concentration or amount of ions, analytes, molecules, minerals, or other solutes present in the sample effluents. For example, the first electrical characteristic and the second electrical characteristic can differ when the solution characteristic of the first sample effluent 1102A and the solution characteristic of the second sample effluent differ in their pH.

In one embodiment, the parameter analyzer 114 can assess the susceptibility of the infectious agent 102 to the anti-infective 104 as a binary assessment or a tiered assessment. In another embodiment, a reader or computing device connected or communicatively coupled to the parameter analyzer 114 can assess the susceptibility of the infectious agent 102 to the anti-infective 104 as a binary assessment or a tiered assessment.

The parameter analyzer 114 or the reader communicatively coupled to the parameter analyzer 114 can assess the susceptibility of the infectious agent 102 as either resistant or non-resistant to the anti-infective 104. In this embodiment, the second filter 110B or the second filter surface 126B can comprise a set amount of the anti-infective 104. The parameter analyzer 114 or a reader communicatively coupled to the parameter analyzer 114 can then assess the susceptibility of the infectious agent 102 as either resistant or non-resistant based on any detected differences in the first electrical characteristic and the second electrical characteristic or any detected differences in the change in the first electrical characteristic and the change in the second electrical characteristic.

The parameter analyzer 114 or the reader communicatively coupled to the parameter analyzer 114 can assess the susceptibility of the infectious agent 102 as not resistant to the anti-infective 104 when the parameter analyzer 114 or the reader fails to detect a difference or a statistically significant difference between the first electrical characteristic and the second electrical characteristic or a statistically significant difference between the change in the first electrical characteristic and the change in the second electrical characteristic. More specifically, a statistically significant difference in the electrical characteristic can be a difference exceeding a threshold value.

In other embodiments, the parameter analyzer 114 or the reader communicatively coupled to the parameter analyzer 114 can assess the level of susceptibility of the infectious agent 102 on a tiered scale. For example, the parameter analyzer 114 or the reader communicatively coupled to the parameter analyzer 114 can assess the susceptibility of the infectious agent 102 as being resistant, mildly susceptible, or susceptible to the anti-infective 104. In these embodiments, additional filter surfaces, including a third filter surface, can be used which comprise anti-infectives 104 of different concentrations. While three categories of susceptibility are discussed, it should be understood by one of ordinary skill in the art that four or greater categories of susceptibility or four or more filters can be used to assess the level of susceptibility of the infectious agent 102 to differing concentrations of the anti-infective 104.

The parameter analyzer 114 can also have or be connected to a display 113 or display component configured to provide a result of the detection or a read-out of the electrical characteristic of the first sensing device 800A, the second sensing device 800B, or a combination thereof. In some embodiments, the parameter analyzer 114 can be a mobile device, a handheld device, a tablet device, or a computing device such as a laptop or desktop computer and the display 113 can be a mobile device display, a handheld device display, a tablet display, or a laptop or desktop monitor.

In one embodiment, the parameter analyzer 114 can display a result indicating the level of susceptibility of the infectious agent 102 in the fluid sample 124 via the display 113. In another embodiment, the parameter analyzer 114 can wirelessly communicate a result indicating the presence of an infectious agent 102 in the fluid sample 124 to a computing device having the display 113.

Figure 12:
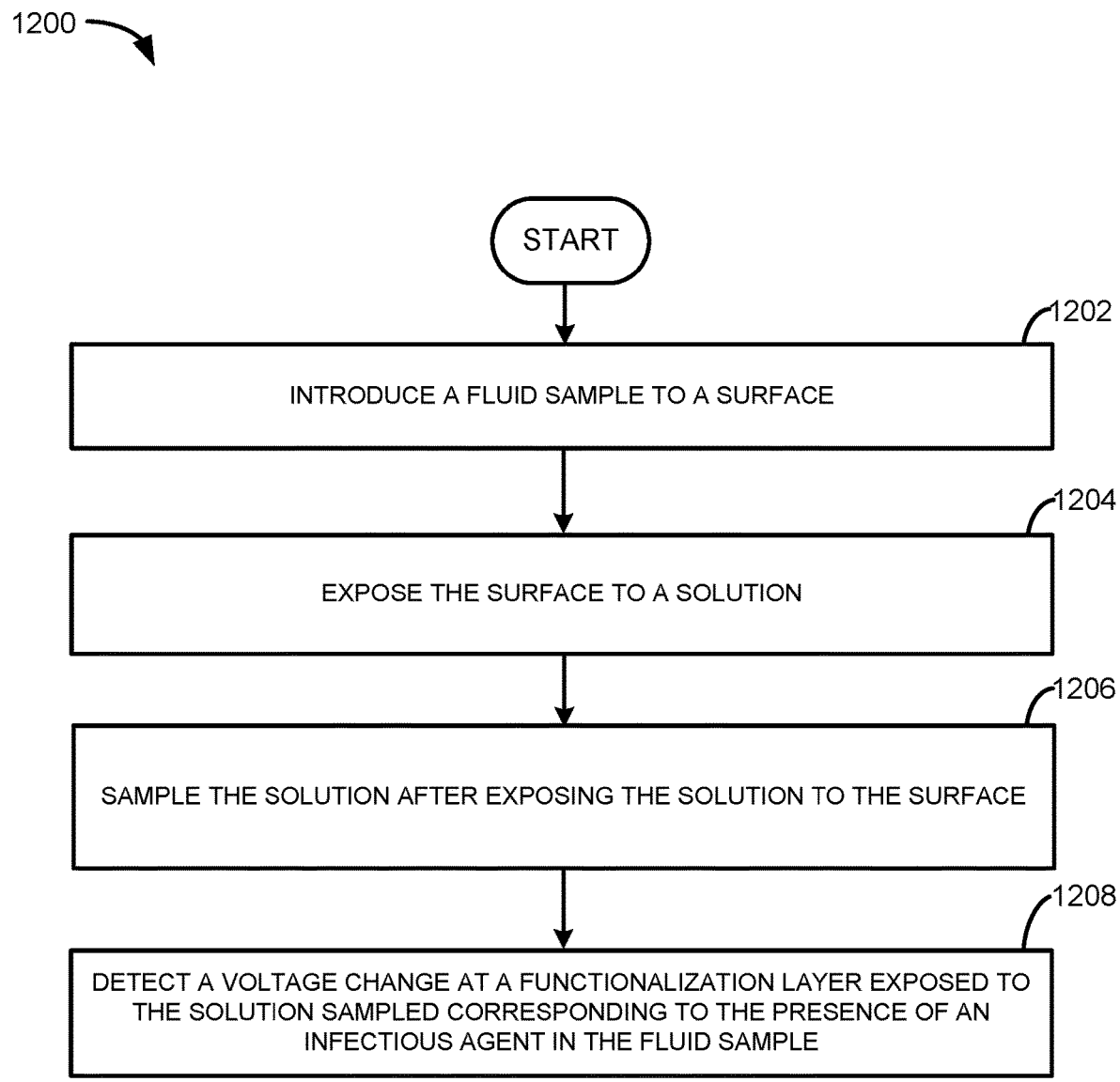
FIG. 12 illustrates one embodiment of a method for detecting infectious agents in a fluid sample.

FIG. 12 illustrates a method 1200 of detecting an infectious agent 102 in a fluid sample 124. The method 1200 can include introducing a fluid sample 124 to a surface, such as the filter surface 126, in a step 1202. The filter surface 126 can isolate, trap, or otherwise contain the infectious agent 102 when a fluid sample 124 carrying or comprising the infectious agent 102 is introduced to the filter surface 126. The method 1200 can also include exposing the surface to a solution, such as the nutrient solution 130, in a step 1204. The method 1200 can further include sampling the solution after exposing the surface to the solution in step 1206. Sampling the solution can include sampling the effluent or outflow of the solution, such as the sample effluent 134. Sampling the solution can also involve separating the solution from the surface so the solution is not in fluid communication or contact with the surface, the infectious agent 102 on the surface, or a combination thereof when sampled.

The method 1200 can also include detecting a change in an electrical characteristic of a sensing device exposed to the solution sampled corresponding to the presence of the infectious agent 102 in the fluid sample 124 in step 1208. When the sensing device is an electrochemical cell such as the sensing device 116, detecting the change in the electrical characteristic comprises determining a voltage change at a functionalization layer covering a working electrode of the electrochemical cell. The functionalization layer can be exposed to the solution sampled and the voltage change can be determined with respect to a reference electrode, such as the external reference electrode 202 of FIG. 2A or the on-chip reference electrode 216 of FIG. 2B, also exposed to the solution sampled.

Figure 13:
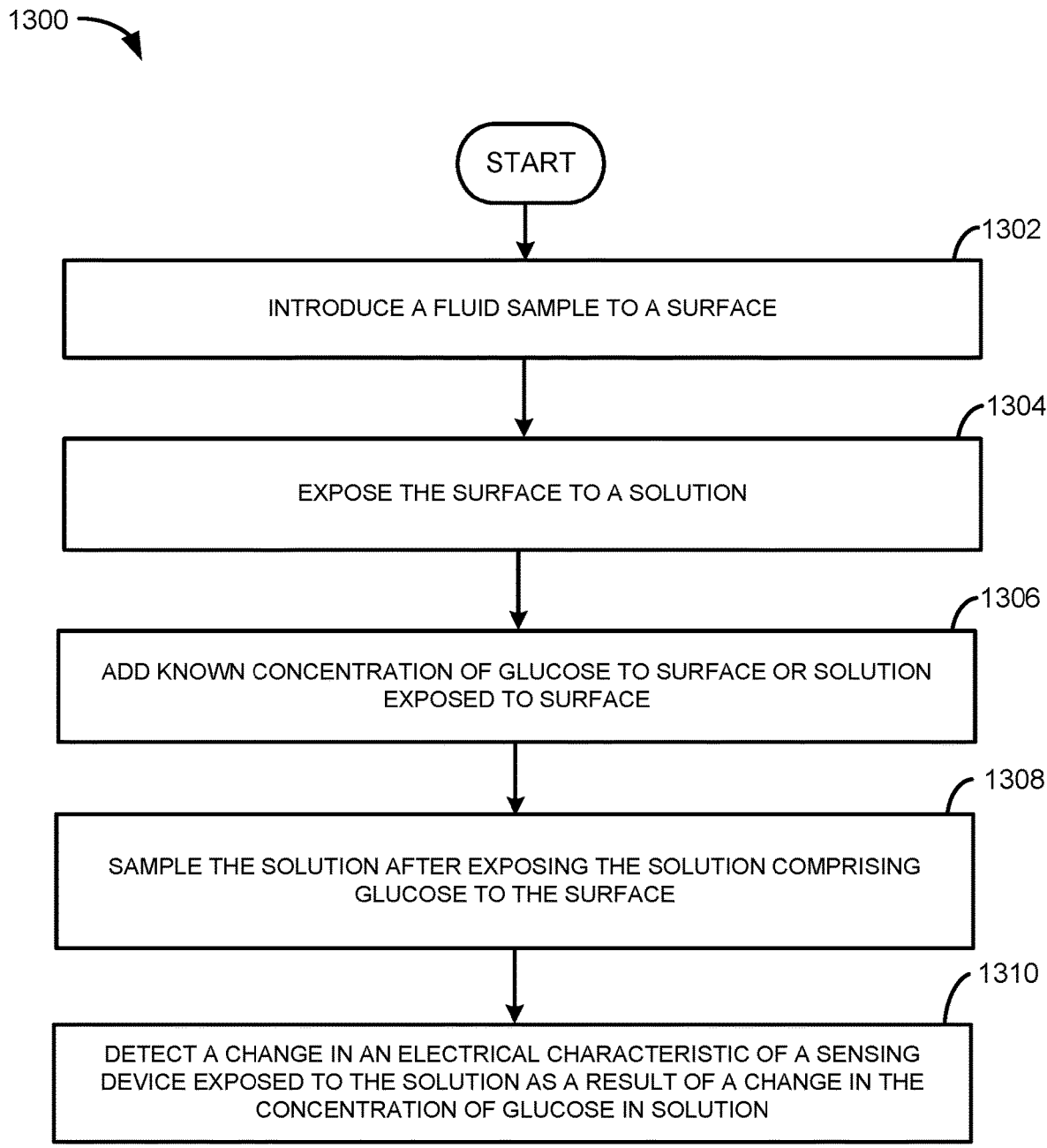
FIG. 13 illustrates one embodiment of a method for detecting infectious agents in a fluid sample.

FIG. 13 illustrates a method 1300 of detecting an infectious agent 102 in a fluid sample 124. The method 1300 can include introducing a fluid sample 124 to a surface, such as the filter surface 126, in a step 1302. The filter surface 126 can isolate, trap, or otherwise contain the infectious agent 102 when a fluid sample 124 carrying or comprising the infectious agent 102 is introduced to the filter surface 126. The method 1300 can also include exposing the surface to a solution, such as the nutrient solution 130, in step 1304.

The method 1300 can also include adding a known concentration of glucose to the solution or the surface exposed to the solution in a step 1306. The method 1300 can further include incubating the solution or surface with the added glucose. The method 1300 can also include sampling the solution comprising glucose in step 1308. Sampling the solution can include sampling the effluent or outflow of the solution comprising glucose exposed to the surface, such as the sample effluent 504. Sampling the solution can also involve separating the solution comprising glucose from the surface so the solution comprising glucose is not in fluid communication or contact with the surface, the infectious agent 102 on the surface, or a combination thereof when sampled.

The method 1300 can also include detecting a change in an electrical characteristic of a sensing device exposed to the glucose solution sampled corresponding to the presence of the infectious agent 102 in the fluid sample 124 in step 1310. When the sensing device is a glucose sensor, such as the sensing device 500, the change in the electrical characteristic is caused by a change in the glucose concentration of the solution sampled.

Figure 14:
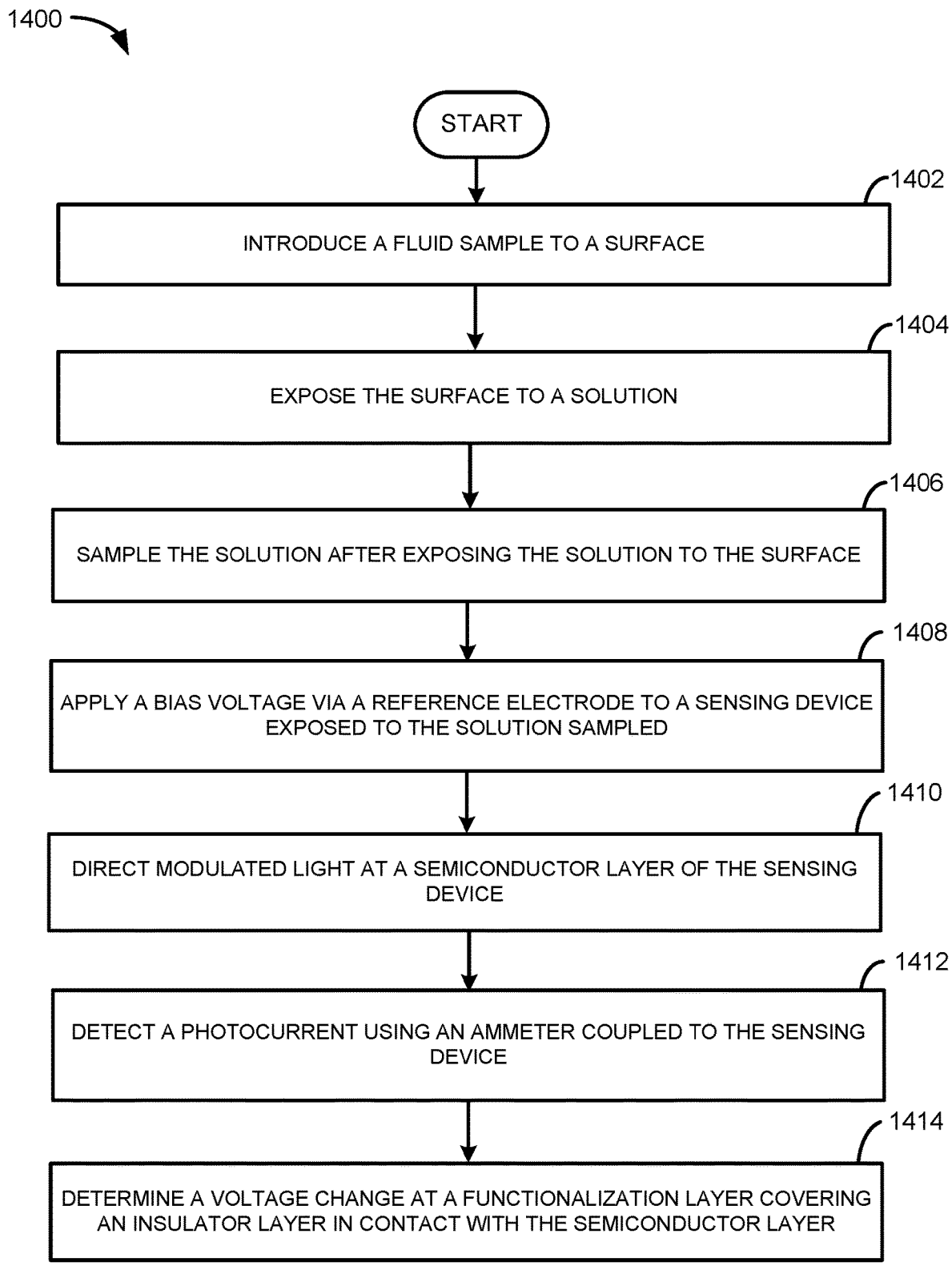
FIG. 14 illustrates another embodiment of a method for detecting infectious agents in a fluid sample.

FIG. 14 illustrates a method 1400 of detecting an infectious agent 102 in a fluid sample 124. The method 1400 can include introducing a fluid sample 124 to a surface, such as the filter surface 126, in step 1402. The filter surface 126 can isolate, trap, or otherwise contain the infectious agent 102 when a fluid sample 124 carrying or comprising the infectious agent 102 is introduced to the filter surface 126. The method 1400 can also include exposing the surface to a solution, such as the nutrient solution 130, in step 1404. The method 1400 can further include sampling the solution after exposing the surface to the solution in step 1406. Sampling the solution can include sampling the effluent or outflow of the solution, such as the sample effluent 134. Sampling the solution can also involve separating the solution from the surface so the solution is not in fluid communication or contact with the surface, the infectious agent 102 on the surface, or a combination thereof when sampled.

The method 1400 can also include applying a bias voltage via a reference electrode to a sensing device, such as the sensing device 800, exposed to the solution sampled in step 1408. The method 1400 can also include directing light using a modulated light source at a semiconductor layer, such as the semiconductor layer 906 of FIG. 9, of the sensing device in step 1410. The method can also include detecting a photocurrent using an ammeter coupled to the sensing device in step 1412. The method can further include determining a voltage change at a functionalization layer, such as the functionalization layer 902 of FIG. 9, covering an insulator layer, such as the insulator layer 904, in contact with the semiconductor layer of the sensing device. The voltage change, or another change in the electrical characteristic, of the sensing device exposed to the solution sampled can correspond to the presence of an infectious agent 102 in the fluid sample 124.

FIG. 15 illustrates a method 1500 for detecting a susceptibility of an infectious agent 102 to an anti-infective 104. The method 1500 can include introducing a fluid sample 124 to a first surface, such as the first filter surface 126A, and a second surface, such as the second filter surface 126B, in a step 1502. The method 1500 can also include exposing the first surface to a first solution, such as the nutrient solution 130, in a step 1504. The first surface can comprise the infectious agent 102 when the infectious agent 102 is present in the fluid sample 124.

The method 1500 can also include exposing the second surface to a second solution, such as additional instances of the nutrient solution 130 in a step 1506. The second surface can comprise an anti-infective 104. The second surface can also comprise the infectious agent 102 when the infectious agent 102 is present in the fluid sample 124.

The method 1500 can also include sampling the first solution after exposing the first solution to the first surface in step 1508. Sampling the first solution can include sampling the effluent or outflow of the first solution, such as the first sample effluent 1102A. In one embodiment, sampling the first solution can also involve separating the first solution from the first surface so the first solution is not in fluid communication with the first surface, the infectious agent 102 on the first surface, or a combination thereof when sampled. The method 1500 can also include sampling the second solution after exposing the second solution to the second surface in step 1510. Sampling the second solution can include sampling the effluent or outflow of the second solution, such as the second sample effluent 1102B. In one embodiment, sampling the second solution can also involve separating the second solution from the second surface so the second solution is not in fluid communication with the second surface, the infectious agent 102 on the second surface, or a combination thereof when sampled.

The method 1500 can also include monitoring a first electrical characteristic of a first sensing device, such as the first sensing device 116A, the first sensing device 500A, or the first sensing device 800A, exposed to the first solution sampled in step 1512. The method 1500 can also include monitoring a second electrical characteristic of a second sensing device, such as the second sensing device 116B, the second sensing device 500B, or the second sensing device 800B exposed to the second solution sampled in step 1514. The method 1500 can further include comparing the first electrical characteristic and the second electrical characteristic to assess the susceptibility of the infectious agent 102 to the anti-infective 104 in step 1516.

FIG. 16 illustrates another method 1600 for detecting a susceptibility of an infectious agent 102 to an anti-infective 104. The method 1600 can include introducing a fluid sample 124 to a first surface, such as the first filter surface 126A, and a second surface, such as the second filter surface 126B, in a step 1602. The method 1600 can also include exposing the first surface to a first solution, such as the nutrient solution 130, in a step 1604. The first surface can comprise the infectious agent 102 when the infectious agent 102 is present in the fluid sample 124.

The method 1600 can also include exposing the second surface to a second solution, such as additional instances of the nutrient solution 130 in a step 1606. The second surface can comprise an anti-infective 104. The second surface can also comprise the infectious agent 102 when the infectious agent 102 is present in the fluid sample 124.

The method 1600 can also include sampling the first solution after exposing the first solution to the first surface in step 1608. Sampling the first solution can include sampling the effluent or outflow of the first solution, such as the first sample effluent 1102A. In one embodiment, sampling the first solution can also involve separating the first solution from the first surface so the first solution is not in fluid communication with the first surface, the infectious agent 102 on the first surface, or a combination thereof. The method 1600 can also include sampling the second solution after exposing the second solution to the second surface in step 1610. Sampling the second solution can include sampling the effluent or outflow of the second solution, such as the second sample effluent 1102B. In one embodiment, sampling the second solution can also involve separating the second solution from the second surface so the second solution is not in fluid communication with the second surface, the infectious agent 102 on the second surface, or a combination thereof.

The method 1600 can also include monitoring a first electrical characteristic of a sensing device, such as the first sensing device 116A, the first sensing device 500A, or the first sensing device 800A, exposed to the first solution sampled in step 1612. The method 1600 can also include monitoring a second electrical characteristic of the sensing device exposed to the second solution sampled in step 1614. The method 1600 can further include comparing the first electrical characteristic and the second electrical characteristic to assess the susceptibility of the infectious agent 102 to the anti-infective 104 in step 1616.

The flowcharts or process flows depicted in FIGS. 12-16 do not require the particular order shown to achieve the desired result and certain steps or processes may occur in parallel.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. A system of assessing a susceptibility of an infectious agent to an anti-infective, the system comprising:
   a fluid delivery device configured to introduce a fluid sample to a first surface and a second surface;
   the same fluid delivery device or another fluid delivery device configured to introduce a first solution to the first surface comprising the infectious agent;
   the same fluid delivery device or another fluid delivery device configured to introduce a second solution to the second surface comprising the infectious agent, wherein at least one of the second surface and the second solution comprises an anti-infective;
   a first sensing device configured to be exposed to a sample of the first solution after the first solution is exposed to the first surface, wherein a first electrical characteristic of the first sensing device is monitored;
   a second sensing device configured to be exposed to a sample of the second solution after the second solution is exposed to the second surface, wherein a second electrical characteristic of the second sensing device is monitored; and
   a parameter analyzer configured to compare the first electrical characteristic, including a change in the first electrical characteristic, with the second electrical characteristic, including any changes in the second electrical characteristic, wherein any differences between the first electrical characteristic and the second electrical characteristic, or lack thereof, is used to assess the susceptibility of the infectious agent to the anti-infective.

2. The system of claim 1, wherein the first sensing device is a first electrochemical cell and wherein the first electrical characteristic of the first sensing device is monitored by determining a first voltage change at a first functionalization layer exposed to the first solution sampled, wherein the first voltage change is with respect to a voltage at a first reference electrode also exposed to the first solution sampled and the first functionalization layer covers a first working electrode of the first electrochemical cell; and wherein the second sensing device is a second electrochemical cell and wherein the second electrical characteristic of the second sensing device is monitored by determining a second voltage change at a second functionalization layer exposed to the second solution sampled, wherein the second voltage change is with respect to a voltage at a second reference electrode also exposed to the second solution sampled and the second functionalization layer covers a second working of the second electrochemical cell.

3. The system of claim 1, wherein the first reference electrode is a first on-chip reference electrode separated by a first insulator from the first working electrode and the second reference electrode is a second on-chip reference electrode separated by a second insulator from the second working electrode.

4. The system of claim 1, further comprising adding a known concentration of an analyte to the first solution before sampling the first solution and adding the same known concentration of the analyte to the second solution before sampling the second solution.

5. The system of claim 4, wherein the first sensing device is a first analyte sensor and the second sensing device is a second analyte sensor.

6. The system of claim 5, wherein the first analyte sensor comprises a first working electrode, a first reference electrode, and a first counter electrode.

7. The system of claim 5, wherein the second analyte sensor comprises a second working electrode, a second reference electrode, and a second counter electrode.

8. The system of claim 5, wherein the parameter analyzer is configured to compare the first electrical characteristic and the second electrical characteristic by determining a difference between the first electrical characteristic and the second electrical characteristic and wherein the difference between the first electrical characteristic and the second electrical characteristic is a result of a difference in the concentration of the analyte in the first solution sampled and the concentration of the analyte in the second solution sampled.

9. The system of claim 1, wherein the first sensing device is a first light-addressable potentiometric (LAP) sensor and wherein the first electrical characteristic of the first sensing device is monitored by:
applying a first bias voltage via a first reference electrode of the first LAP sensor exposed to the first solution sampled;
directing a first modulated light at a first semiconductor layer of the first LAP sensor;
detecting a first photocurrent using a first ammeter coupled to the first LAP sensor; and
determining a first voltage change at a first functionalization layer of the first LAP sensor exposed to the first solution sampled.

10. The system of claim 1, wherein the second sensing device is a second LAP sensor and wherein the second electrical characteristic of the second sensing device is monitored by:
applying a second bias voltage via a second reference electrode of the second LAP sensor exposed to the second solution sampled;
directing a second modulated light at a second semiconductor layer of the second LAP sensor;
detecting a second photocurrent using a second ammeter coupled to the first LAP sensor; and
determining a second voltage change at a second functionalization layer of the second LAP sensor exposed to the second solution sampled.

11. The system of claim 1, wherein the first surface is a filter surface or a well surface.

12. The system of claim 11, wherein the second surface is separated from the first surface and is another instance of the filter surface or the well surface.

13. The system of claim 11, wherein the filter surface is configured to trap the infectious agent on the first surface.

14. The system of claim 1, wherein at least one of the first surface and the second surface is a high-capacity filter.

15. The system of claim 1, wherein at least one of the first surface and the second surface comprises pores of a similar pore size.

16. The system of claim 1, wherein the parameter analyzer is configured to compare the first electrical characteristic with the second electrical characteristic by determining a difference between the first electrical characteristic and the second electrical characteristic and wherein the difference between the first electrical characteristic and the second electrical characteristic is a result of a difference in a solution characteristic of the first solution and the second solution.

17. The system of claim 16, wherein the difference in the solution characteristic of the first solution and the second solution is a difference in at least one of a molecular count, a concentration of an ion, and a solution temperature.

18. The system of claim 1, wherein the infectious agent is a bacteria, a fungus, a virus, or a prion.

19. The system of claim 1, wherein at least one of the first sensing device and the second sensing device is housed by a protective chamber and the protective chamber is at least one of an electrically isolated environment, a temperature-controlled chamber, and a light-controlled chamber.

20. The system of claim 1, further comprising a pump configured to direct the first solution to the first surface or direct the second solution to the second surface.

21. The system of claim 1, wherein the first reference electrode is a first external reference electrode and the second reference electrode is a second external electrode.

* * * * *